(12) United States Patent
Giap et al.

(10) Patent No.: US 10,220,181 B2
(45) Date of Patent: Mar. 5, 2019

(54) VIRTUAL REALITY MEDICAL APPLICATION SYSTEM

(71) Applicant: Virtual Reality Medical Applications, Inc., Rancho Santa Fe, CA (US)

(72) Inventors: Huan Giap, San Diego, CA (US); Garland Wong, San Diego, CA (US)

(73) Assignee: VIRTUAL REALITY MEDICAL APPLICATIONS, INC

( * ) Notice: Subject to any disclaimer, the term of this patent is extended or adjusted under 35 U.S.C. 154(b) by 83 days.

(21) Appl. No.: 14/641,302

(22) Filed: Mar. 6, 2015

(65) Prior Publication Data

US 2015/0306340 A1 Oct. 29, 2015

Related U.S. Application Data

(60) Provisional application No. 61/949,196, filed on Mar. 6, 2014.

(51) Int. Cl.
| | |
|---|---|
| *A61B 1/00* | (2006.01) |
| *A61M 21/00* | (2006.01) |
| *A61B 5/055* | (2006.01) |
| *A61B 5/107* | (2006.01) |
| *A61B 5/11* | (2006.01) |

(Continued)

(52) U.S. Cl.
CPC ........... *A61M 21/00* (2013.01); *A61B 1/0005* (2013.01); *A61B 5/055* (2013.01); *A61B 5/107* (2013.01); *A61B 5/11* (2013.01); *A61B 5/70* (2013.01); *A61B 6/03* (2013.01); *A61B 6/037* (2013.01); *A61B 6/46* (2013.01); *A61B 6/461* (2013.01); *A61N 5/1001* (2013.01); *A61N 5/1049* (2013.01); *A61N 5/1068* (2013.01);

*G06F 19/00* (2013.01); *G06F 19/3481* (2013.01); *G06T 19/006* (2013.01); *G16H 40/63* (2018.01); *A61B 5/0046* (2013.01); *A61B 5/021* (2013.01); *A61B 5/024* (2013.01); *A61B 5/02055* (2013.01); *A61B 5/0402* (2013.01); *A61B 5/0476* (2013.01); *A61B 5/05* (2013.01); *A61B 5/1114* (2013.01); *A61B 5/1176* (2013.01); *A61B 5/704* (2013.01); *A61B 5/744* (2013.01); *A61B 6/04* (2013.01); *A61B 6/0492* (2013.01);

(Continued)

(58) Field of Classification Search
CPC ......... A61M 21/00; A61B 90/37; A61B 5/021
See application file for complete search history.

(56) References Cited

U.S. PATENT DOCUMENTS

| | | | | |
|---|---|---|---|---|
| 2002/0023652 A1* | 2/2002 | Riaziat | ................. | A61N 5/1049 128/897 |
| 2006/0074305 A1* | 4/2006 | Mostafavi | .............. | A61B 6/032 600/428 |

(Continued)

FOREIGN PATENT DOCUMENTS

| | | |
|---|---|---|
| WO | WO0129799 A2 | 4/2001 |
| WO | WO2012145430 A1 | 10/2012 |
| WO | WO2013054257 A1 | 4/2013 |

*Primary Examiner* — Joseph M Dietrich
(74) *Attorney, Agent, or Firm* — Gary L. Eastman, Esq.; Eastman McCartney Dallmann LLP

(57) ABSTRACT

Systems and methods are disclosed for monitoring a patient by positioning the patient for a predetermined medical mission; sensing biometric and physical conditions of a patient during the mission, and displaying a multimedia interaction with the patient to keep the patient in a predetermined position to improve efficacy of a medical mission.

12 Claims, 22 Drawing Sheets

(51) Int. Cl.

| | |
|---|---|
| *A61B 5/00* | (2006.01) |
| *A61B 6/03* | (2006.01) |
| *A61N 5/10* | (2006.01) |
| *G06T 19/00* | (2011.01) |
| *A61B 6/00* | (2006.01) |
| *G06F 19/00* | (2018.01) |
| *G16H 40/63* | (2018.01) |
| *A61B 5/05* | (2006.01) |
| *A61B 5/021* | (2006.01) |
| *A61B 5/024* | (2006.01) |
| *A61B 5/0402* | (2006.01) |
| *A61B 5/0476* | (2006.01) |
| *A61B 5/0205* | (2006.01) |
| *A61B 6/04* | (2006.01) |
| *A61B 5/1171* | (2016.01) |

(52) U.S. Cl.
CPC ................ *A61B 2562/0219* (2013.01); *A61M 2021/005* (2013.01); *A61M 2021/0027* (2013.01)

(56) References Cited

U.S. PATENT DOCUMENTS

| | | | |
|---|---|---|---|
| 2010/0115548 A1* | 5/2010 | Leyvi | G09B 5/06 725/34 |
| 2010/0238362 A1 | 9/2010 | Hughes et al. | |
| 2010/0249494 A1 | 9/2010 | Yoshizawa | |
| 2011/0072367 A1* | 3/2011 | Bauer | G06F 3/04815 715/757 |
| 2012/0212406 A1* | 8/2012 | Osterhout | G02B 27/017 345/156 |

\* cited by examiner

VIRTUAL REALITY MEDICAL APPLICATION SYSTEM

RELATED APPLICATIONS

This application claims the benefit of priority to U.S. Provisional Patent Application Ser. No. 61/949,196 filed Mar. 6, 2014, the content of which is fully incorporated herein incorporated by reference.

FIELD OF THE INVENTION

The present invention relates generally to medical treatment apparatus. The present invention is more particularly, though not exclusively, useful as a patient monitoring system that monitors both the biometric and physical condition of a patient, and provides a virtual reality interface to that patient to improve the tolerance and efficacy of the medical treatment. The present invention is most particularly useful as a virtual reality environment which interfaces to medical treatment apparatus and with medical service providers to decrease the discomfort, anxiety and pain of a patient during a procedure, such as radiation therapy, MRI imaging, conoloscopy or biopsy.

BACKGROUND OF THE INVENTION

Radiation causes cellular degradation due to damage to DNA and other key molecular structures within the cells in various tissues. It was discovered that with controlled amounts of radiation, the effects caused by radiation can be utilized to treat certain diseases. With the use of radiation, several previously untreatable diseases have been able to be successfully treated using radiation therapies. However, along with the curative effects of radiation are negative side effects. The prolonged exposure to radiation include both immediate and delayed side effects. The immediate side effects of radiation exposure include nausea and vomiting, headaches, fevers, and skin burns, whereas the delayed effects could include fatigue, weakness, hemorrhaging, leukopenia, epilation and other various side effects. Additionally, the prolonged overexposure of unnecessary radiation may cause more serious complications and may lead to mortality. Due to the serious side effects of utilizing radiation as a form of medical treatment, numerous steps have been taken to limit the exposure of radiation to healthy tissue by focusing the radiation solely on the diseased tissue.

External beam radiation therapy, the most common form of radiation therapy, is the application of radiation at a particular part of the body with the use of an external source of radiation. External beam radiation therapy directs concentrated radiation to the treatment area from outside of the body. To minimize the exposure of the concentrated radiation to healthy tissue, the concentrated radiation beam is precisely controlled by the use of mechanical hardware and computer software. Current technology allows radiation to be precisely focused on the diseased tissue occupying a minuscule area on a larger healthy tissue. The use of multiple low-radiation beams focusing on an area of diseased tissue at different approach angles creates a single, focused and concentrated radiation beam. This exposes the surrounding healthy tissue to lower levels of radiation due to the use of multiple low-radiation beams. The advancements in technology have allowed the precise delivery of the concentrated beams to a diseased tissue while minimizing the exposure to the surrounding healthy tissue.

The course of radiation treatment typically consists of multiple daily treatments (20 to 40) over a course of 4 to 8 weeks, and each day the radiation treatment is given over a period of about 15-30 minutes. Although the directed radiation beam precisely delivers the radiation to diseased tissue, its frame of reference is to a stationary patient and traditionally does not take into account the natural and unnatural movements of a patient during that 15-30 minute treatment. In more advanced techniques where higher levels of radiation are used, in order to allow the patients to fully benefit from the procedure and minimize its side effects, the delivery of the radiation must be precise, requiring radiation alignment accuracies in range of millimeter. Due to the fact that the radiation dose is delivered over a period of 15-30 minutes during which patient must remain still. The slight movement of a patient during a treatment will alter the point of delivery of the concentrated radiation beam, therefore reducing the exposure of radiation to the diseased tissue while increasing the exposure of radiation to the healthy tissue. The treatments then become less effective which would require additional treatment, further exposing the surrounding healthy tissue to unneeded radiation or other treatment types. The patient's movements must be eliminated or minimized to ensure proper delivery of radiation to diseased tissue and minimize the exposure to healthy tissue.

Currently, there are two major ways to monitor movement of the patients. One is a technician must constantly watch the patient via a in-room video to make sure they are not moving for up to a 30 minute period. This is error prone since it is subject to the technician interpretation of movement.

In order to minimize the movements, patients are traditionally subject to invasive and uncomfortable methods of immobilization. Methods include utilizing stabilizing frames attached to the body, stabilizing body casts or plastic molds, and internal spacers inserted within a patient's body to stabilize the diseased tissue. To control the tolerance of a patient's movement, tight clearance is required. This may cause discomfort and pain as the patient is tightly held in a single position for periods of up to 30 minutes for a single treatment. The physical restriction of the movements of the patient may cause or increase the levels of anxiety, resulting in heavier and quicker breathing. This is particularly important when treating diseased tissue that moves with any bodily function associated with breathing or involuntary cough. For children with cancer that require radiation treatment and cannot cooperate to remain still, they require daily general anesthesia, where they have to be put to sleep with invasive sedative medications via an intravenous route and require oxygen through their nose and mouth. This daily procedure typically costs an additional $5,000 to 6,000 per day, requires additional medical staff (such as anesthesiologists and nurses), medical equipment, and results in a longer treatment time. Besides being invasive, treatment involving general anesthesia requires an additional 3-5 hours per day for these young patients due to induction and recovery time.

Patients generally prefer to be unrestrained. In instances where the use of mechanical stabilization devices is undesirable or not feasible, the patient must refrain from moving, including the momentary cessation of breathing. To ensure the patient has not moved from their initial position and ensure proper alignment of the radiation with the diseased tissue, a technician must continually monitor the movements of the patient. The technician may be error prone as it requires the technician's interpretation of whether the patient has moved a distance as little as few centimeters. Alternatively, the precise monitoring of a patient's bodily movement can be monitored using real-time 3-dimensional surface imaging techniques. Using real-time 3-dimensional surface imaging techniques, the patient's current body position is continually cross-referenced with an ideal reference image, which is used to calculate the coordinates to deliver radiation. If movement is detected the technician is alerted and the technician alerts the patient not to move, eliminating the need for a technician's judgment of a patient's body position.

The current standard way to monitor movement of the patients requires a technician to constantly watch the patient via an in-room video to make sure they are not moving for up to a 30 minute period. This is error prone since it is subject to the technician interpretation of movement; it only shows only gross movement or body positioning. This system does not allow patient's participation and monitoring of his/her movement, and patients has no control or awareness. If the technician sees body movement, he/she has to re-enter to treatment room to re-adjust patient position to match the reference position, and this adds additional time to the treatment.

One system (the Varian® Real-time Position Management™ or RPM), a currently existing medical device (VisionRT), uses real-time 3-D surface imaging incorporating an in-room camera to monitor movement. This monitoring is achieved by comparing the live three dimensional patient surface images with reference images and the system provides the difference between the 2 image sets to the technician. When movement is detected and the workstation will alert the technician, the technician alerts the patient not to move. There is some delay (deadtime) between time the movement is detected and the technician instruction to patient. This approach is even less effective when patients are experiencing pain and uncontrolled movements, as well as those with hearing impairment or are simply too young to understand the technician's instructions.

The control of radiation exposure is particularly challenging for children because children are naturally more anxious than adults. Staying still for prolonged periods of times for the treatment is a difficult proposition for children and the use of mechanical stabilization devices or sedatives is commonly used. The mechanical stabilization devices generally cause additional anxiety in children as they are bound and immobilized, resulting in crying, screaming, and minute movements as they struggle to become free. The use of sedatives, although effective to immobilize, comes with medical risk of the sedative medications, costs (up to several thousands dollars per treatment), and extended induction and recovery time (3-5 hours per treatment). This risk is repeated every day, 5 days per week, for period of 3-6 weeks.

In light of the above, it would be advantageous to provide an apparatus and method to decrease the movement of patients undergoing radiotherapy. It would further be advantageous to provide an apparatus and method to decrease the movement of patients undergoing radiotherapy which does not use physical restraints or chemical sedatives to immobilize a patient. It would further be advantageous to provide an apparatus and method to decrease the movement of patients undergoing radiotherapy which is non-invasive and comfortable. It would further be advantageous to provide an apparatus and method to decrease the movement of patients undergoing radiotherapy which monitors the real-time position of a patient and relays the information to the patient about the specific area of the body and allows patient to make adjustment to get back to the reference or desired position. It would further be advantageous to provide an apparatus and method to decrease the movement of patients undergoing radiotherapy which alerts a third party (operator or technician) of excessive movement outside a set range and which part of the body. It would further be advantageous to provide an apparatus and method to assure the safely to patients undergoing radiotherapy which send an interrupt signal instantly to the radiation equipment to pause the radiation beam due to excessive movement outside a set range. It would further be advantageous to provide an apparatus and method to decrease the movement of patients undergoing radiotherapy which provides a virtual reality system which visualizes the patient's current physical and biometric measurements and allows for the real-time adjustment of their physical and biometric measurements in response.

SUMMARY OF THE INVENTION

The Virtual Reality Medical Application System of the present invention is a medical system including a combination of hardware and software that will improve a patient's ability to remain still during medical procedures that require a patient to not move. The system includes three primary components: the hardware component; the software component; and a sensor component. The hardware component consists of a three dimensional (3-D) goggle to provide visual images to patients, noise-cancellation headphone and microphone system to provide 3-way communication between the patient, the healthcare provider, and the Virtual Reality Medical Application System software.

The software component provides a variety of patient specific 3-D games that are controlled by patients, virtual simulation of real life scenery (car racing, hot-air balloon, fish-eye view, etc), and may include real time images of the procedure that a healthcare provider wants to share with patient, such as an inside image of the colon from the colonoscopy. The 3-D games and virtual simulation software will be developed is, in a preferred embodiment, run on linin, and the technician console is a cross platform and runs on Windows, Mac OSX, and Linux in a custom medical-grade computer with input/output ports and storage system.

The sensor component performs two major functions: motion tracking and biofeedback. For motion tracking of the patients, sensors such as gyroscope and accelerometer sensors on the 3-D goggles to detect head motion and one or more video cameras monitor patient body motions. For biofeedback, sensors such as blood pressure, heart rate, EEG, and EKG, among others will help a technician keep informed of the patient condition, and will tend to determine the game play mechanics.

Alternatively, motion may be detected using a motion sensing device, capable of three-dimensional motion detection. One such sensor is commercially available as the Kinect sensor. Kinect builds on software technology developed internally by Rare, a subsidiary of Microsoft Game Studios owned by Microsoft, and on range camera technology by Israeli developer PrimeSense, which developed a system that can interpret specific gestures, making completely hands-free control of electronic devices possible by using an infrared projector and camera and a special microchip to track the movement of objects and individuals in three dimensions. This 3D scanner system, often called Light Coding, employs a variant of image-based 3D reconstruction.

The Kinect sensor is a horizontal bar connected to a small base with a motorized pivot and is designed to be positioned lengthwise above or below the video display. The device features an "RGB camera, depth sensor and multi-array microphone running proprietary software" which provide full-body 3D motion capture, facial recognition and voice recognition capabilities. Kinect sensor's microphone array enables its attached devices, such as an Xbox 360, to conduct acoustic source localization and ambient noise suppression, allowing for things such as headset-free party chat over Xbox Live.

The depth sensor consists of an infrared laser projector combined with a monochrome CMOS sensor, which captures video data in 3D under any ambient light conditions. The sensing range of the depth sensor is adjustable, and Kinect software is capable of automatically calibrating the sensor based on gameplay and the player's physical environment, accommodating for the presence of furniture or other obstacles.

Described by Microsoft personnel as the primary innovation of Kinect, the software technology enables advanced gesture recognition, facial recognition and voice recognition. According to information supplied to retailers, Kinect is capable of simultaneously tracking up to six people, including two active players for motion analysis with a feature extraction of 20 joints per player. However, PrimeSense has stated that the number of people the device can "see" (but not process as players) is only limited by how many will fit in the field-of-view of the camera.

The Virtual Reality Medical Application System of the present, in a preferred embodiment, is particularly suited for use with patients undergoing radiation therapy, but may be used to cover patients undergoing brachytherapy, Magnetic Resonance Imaging (MRI), angiography, biopsy procedures and endoscopy such as bronchoscopy or colonoscopy, for example. In addition to keeping the technician informed of the status of the patient, the Virtual Reality Medical Application System of the present invention also helps the patient relax and also distract from the anxiety and pain of these procedures. The visual and audio system allows the healhcare provider to share the clinical information to the patient (e.g., the images of abnormal findings from the colonoscopy)

The Virtual Reality Medical Application System of the present invention also provides benefits in for patient setup before each radiation treatment. When a patient comes in every day for the radiation treatment, he/she must be positioned in exactly the same position as the reference or planned position. This is performed by using restrained devices, adjustment by operators/technicians, and then verified by using invasive X-ray images or Computed Tomography (CT scan). All of these add times (5-10 minutes), cost (hundred of dollars), and unnecessary radiation exposure to patients. The Virtual Reality Medical Application System of the present invention uses body sensor to detect the 3-D body position, comparing to the reference or desired position, and give feedback to patients via a game avatar to instruct patient to make adjustment on a specific body parts on their own to get within the reference position. Therefore, it provides a much less expensive, noninvasive (no radiation imaging required), more accurate, and quicker.

The Virtual Reality Medical Application System relies on motion sensors, google, and 3-D game to monitor patients during the radiation treatment and provide instant feedback to patients to remind them staying still via such process as pausing of the game, commands from game character, etc. Since radiation treatment is typically delivered in 15-20 min during which patients must remain still, any unnecessary involuntarily movement will cause radiation to deliver incorrectly to normal structure and missing tumor. Within radiation therapy, the Virtual Reality Medical Application System of the present invention is particularly well suited for use with children with cancer that undergo radiation therapy. There are about 10,000 cases of children cancer in the U.S. every year, and about ½ of these children will undergo radiation therapy daily for several weeks.

Because, kids typically can be very anxious, staying still is a significant problem during these procedures. The alternative to keeping still voluntarily is to sedate them via intravenous sedatives and anesthetic gas. Sedation comes with anesthesia medication risk, costs several thousand dollars per day, and extends daily treatment time from less than an hour to more than 4 to 5 hours per day. The Virtual Reality Medical Application System of the present will be useful because it will reduce the complications that can come from sedating a child, reduce costs since sedation will not be necessary, and speed up the procedure since there is no need to wait for the anesthesia and its recovery.

The Virtual Reality Medical Application System of the present invention is novel and non-obvious because it utilizes a three-dimensional virtual reality game/simulation and sensors to feed the information directly to the patients to help the patient remain still voluntarily. In a preferred embodiment, the patient will play the game wearing a head mounted display or HMD or Head Mounted Display. The HMD will provide a view into the virtual world where the patient can see himself as an avatar. The HMD will also provide motion tracking of the head and a sensor such as a camera will track the movement of the patient's body. When the patient moves in the real world, his avatar will move in the virtual world. Since, the movement is detected by the game, and the patient will immediately see that he is moving in real time, the game will negatively reinforce the patient to not move utilizing game play mechanics. For example, playing a virtual game of hide and seek, where movement and being detected will make you lose the game. This is one example of negative reinforcement. There is also positive reinforcement in that has the player completes various levels by remaining still, he is positively reinforce with an achievement. As he builds more achievements and levels up, he will want to remain still. The virtual reality provided by the goggles and headphone and microphone will help patients remain relaxed by distracting patients from the stressful environment of the treatment room, hence relieve the anxiety.

The Virtual Reality Medical Application System of the present invention also utilizes biofeedback data via sensors such as heart rate, blood pressure, body motion, EKG, EMG, and EEG to enhance the game experience, and to improve the treatment efficacy to the patient. For instance, using the hide and seek game as an example outlined above, when the character seeking for the patient (e.g. his or her avatar) is approaching the avatar's hiding place, if the system detects an increase heart rate or increase blood pressure, the system may have the seeking character retreat from the patient's avatar thus reducing the anxiety level of the patient and thus increasing the odds of the patient not moving.

The three-way communication system allows for continuous communication between patient, the healthcare provider, and the simulated game (software).

In an application of the Virtual Reality Medical Application System of the present invention associated with a radiation, the radiation treatment typically takes about 30 minutes overall. However, during this 30 minute treatment, there is a crucial window of about 10 minutes where the patient should be absolutely still. During this treatment period, the Virtual Reality Medical Application System utilizes innovative game play to keep the patient relatively still for 30 minutes but focus on keeping the patient absolutely still for the crucial time period. In the case of radiation therapy, this is ten minutes. During this critical period, the game play may have heightened requirements for remaining still, coupled with increased scoring rates during this critical period, the gamification of the medical process results in a more effective treatment.

Virtual Reality Medical Application System of the present invention also includes a detection-notification cycle which is automated because the patient receives real time feedback to not move. This reduces the complications caused by human error. For instance, because the patient is immersed in the virtual environment, he cannot see or hear the external environment, including the rather noisy radiation machine or MRI machine. This environmental isolation helps the patient relax and increases their ability to remain still during the procedure. Moreover, the patients immersion in a 3-D world via a HMD has analgesic properties for acute pain, which provides for a reduction in pain perceived by the patient.

The Virtual Reality Medical Application System of the present invention is suitable for a variety of medical applications. For instance, all patients of all ages that receive radiation therapy (including brachytherapy) will have an improved experience using the present invention. There are about 700,000-800,000 patients that receive radiation treatments yearly, and many of these patients are unable to remain still due to pain or anxiety, and which will benefit an improvement in their treatment from the present invention.

The Virtual Reality Medical Application System of the present invention also provides benefits when used with respiratory-gating/tracking of a tumor during radiation therapy. While a patient is receiving radiation treatment for the duration of about 10-15 minutes, there is tumor motion due to respiration, particularly tumors in the lung, breast, and liver. The normal radiation field or treatment portal has to be enlarged to account for this tumor motion, which means more normal structure tissues is being exposed the radiation treatment, hence more treatment side effects. One way to reduce the size of treatment portal or radiation field size is to turn the radiation on only during part of the respiration cycle by having holding their breath for a period of 20-30 seconds. This process is called "respiration gating". With the input from body motion sensor, the present invention facilitates the accurate timing of the radiation beam ("respiration gating") with the respiratory cycle to minimize the effect of tumor motion. The body sensor will send feedback to patients via the headset goggle to instruct patients to hold their breath at the right movement or similar 3-D chest position and send signal to the treatment machine and/or operator to allow the radiation beam to turn on.

Current systems, such as the Varian® Real-time Position Management™ or RPM system, uses an infrared tracking camera and a reflective marker, the system measures the patient's respiratory pattern and range of motion and displays them as a waveform. The gating thresholds are set when the tumor is in the desired portion of the respiratory cycle. These thresholds determine when the gating system turns the treatment beam on and off. The disadvantages of the RPM system are that it relies only on one or two reflective marker (not the whole 3-D chest motion), patients has no control or awareness, and expensive, ranging from $100,000 to $150,000. This system also requires hardware installation into the treatment room.

Another system from Elekta Active Breathhold Coordinator (ABC) system uses spirometer where patient takes a deep breath and breath slowly through their mouth through a tube connected to a spirometer. In this system, the Patient does have control and awareness; however, this system requires patient cooperation, is subjective and uncomfortable since the patient has to hold a snorkel-like mouthpiece in theft mouth air tight for 30-40 minutes. It is also expensive, ranging from $70,000 to $100,000. The Virtual Reality Medical Application System of the present invention also provides benefits to patients using the body sensors and goggle feedback is non-invasive, more objective, easy compliance, patient-controlled, and less expensive system. This system also provides additional sensory input to patients and operators such as oxygen saturation level, heart rate, body temperature, etc.

The Virtual Reality Medical Application System of the present invention also helps patients that undergo medical imaging (MRI, CT, PET) that are too anxious, such as due to claustrophobia, to remain calm. There are estimated 30 millions of patients receiving MRI yearly, and about 5% of these patients have claustrophobia that requires sedation with medication.

The Virtual Reality Medical Application System of the present invention is also useful for patients undergoing minor procedures such as biopsy, cardiac angiography, colonoscopy, endoscopy, bronchoscopy, dental surgery, cosmetic surgeries, interventional radiology procedures, etc. The Virtual Reality Medical Application System of the present invention provides distraction, or escape, from the procedure, thus reducing the need for sedatives and pain medication. The visual and audio system allows the heahlcare provider to share the clinical information to the patient (e.g., the images of abnormal findings from the colonoscopy and share informed consent on what to do with certain findings).

The Virtual Reality Medical Application System of the present invention can also allow patients to visualize the real live images of the procedure that the physicians see on their scope. Since the patients are not sedated, their physicians can communicate and get patients' consent to certain procedures such as decision to biopsy or removal. This is particularly beneficial when the lack of patient consent would prohibit a physician from performing a procedure that would be routine, but were unanticipated at the start of the procedure. Moreover, such active patient participating would eliminate countless repeat medical procedures.

Another use of the Virtual Reality Medical Application System of the present invention includes psychotherapy for patients that are receiving chemotherapy. These patients typically spend 4-8 hours per day in the chemo-infusion rooms or in the hospital receiving their chemotherapy drugs intravenously. The Virtual Reality Medical Application System provides virtual reality escape or "cancer fighting games" that can relieve patients' stress, anxiety, and other cancer related symptoms such as fatigues, nausea, etc.

Also, the Virtual Reality Medical Application System of the present invention is suitable for psychotherapy for patients that have acute pains such as those just have surgery, trauma, such as accidents or burns. The Virtual Reality Medical Application System provides a virtual reality escape or "games" that can relieve patients' stress, anxiety, and other related symptoms, as well as provide psychotherapy for patients that have chronic pain, depression, anxiety disorder, or other personality/mood/affect disorders (autism, OCD, etc. . . . )

Also, the Virtual Reality Medical Application System of the present invention is suitable for psychotherapy for patients that suffer pain from missing arms or legs ("phantom limb pain"). There are approximately 70,000 patients in the U.S. who loose their arms/legs due to military combat or disease such as diabetic or cancer. These patients suffer chronic pain and depression due to the missing limbs.

Another medical device (VisionRT) uses real-time 3-D surface imaging using in-room camera to monitor movement. This monitoring is achieved by comparing the live three dimensional patient surface images with reference images and the system provides the difference between the 2 image sets to the technician. When movement is detected and the workstation will alert the technician, the technician alerts the patient not to move. This system does not allow patient's participation and monitoring of their movement, and patients has no control or awareness. If the technician sees body movement, he/she has to re-enter to treatment room to re-adjust patient position to match the reference position, and this adds additional time to the treatment. This system also requires the monitored body area to be exposed, and it is uncomfortable to some patients (exposing private body areas such as breast or genitals) or due to the low temperature in the treatment room. This approach is even less effective when patients are experiencing pain and uncontrolled movements, as well as those with hearing impairment or are simply too young to understand the technician's instructions. It is also expensive, ranging from $150,000 to $250,000. This system also requires hardware installation into the treatment room.

Similar patient's body position requirement also applies when patient undergoes medical diagnostic imaging such as Computed Tomography (CT) or Computed Axial Tomography (CAT) scan, Magnetic Resonance Imaging (MRI) scan, or Position Emitting Tomography (PET) scan. These diagnostic medical imaging procedures typically lasts about 30-90 minutes, and require patient to lie in a certain position during that period. These imaging devices have a small space and create a feeling of "being trapped" (claustrophobia), it creates anxiety and uncomfortable environment for patient to relax. Millions of people suffer from claustrophobia in U.S. alone, and some could not tolerate these imaging procedures necessary for their medical care or screening. Involuntary body movement will affect the image quality leading to incorrect, uncertain or inconclusive findings. This then often requires repeat imaging or additional imaging procedure or medical procedure which adds cost and inconvenience to patient and health care practitioner. One current option is to ask patient to close their eyes or using a eye patch and listening to music to relax. Another option is to use a video goggle with headphone to show a video or movie to distract the patient. This video goggle does not affect imaging devices function, and typically cost about 30,000 to 40,000 per system, and required some hardware installation to the room.

Patients undergo minor medical procedures such as biopsy, angiography, or medical endoscopy, where a thin flexible fiber optic scope or catheter is inserted into their body to allow clinicians to visually inspect an area of disease, obtain medical imaging using video, photography, ultrasound or X-ray, obtain a biopsy of body tissue, or provide a medical treatment such as cauterization, laser treatment, or putting in a stent to keep an area open. Depending on the organ being examined, these endoscopy procedures can have different names such as bronchoscopy (for lung), colonoscopy (for colon and rectum), proctoscopy (for rectum), anoscopy (anus), cystoscopy (for bladder and urethra), Esophago-Duodeno-Gastroscopy (esophagus, stomach, and small bowel), hysteroscopy (cervix, uterus), endoscopic retrograde cholangiopancreatography or ERCP (for bile duct and pancreas), laryngoscopy (larynx). With the angiography, where catheter is introduced into the patient's blood vessel to make diagnosis and treatment of blood vessel disease such as obstruction. Patients undergoing these procedures require sedation and pain medication via intravenous route and local pain medication (local anesthetics). Occasionally, during these procedures, clinicians want to share the endoscopy findings to patients and getting patients' feedback on further procedure, but not able to due to patients being sedated.

In one aspect, systems and methods are disclosed for a patient monitoring system that monitors both the biometric and physical condition of a patient, and provides a virtual reality interface to that patient to improve the tolerance and efficacy of the medical treatment in a cost-effective manner. This system allows patients' participation and monitoring of their movement, and patients has control and awareness of their body position, and can make adjustment to the reference position. Both the patient and treating technician can see and verify the body positioning. The system is mobile, can be implemented easily and does not require any hardware installation to the treatment room.

In another aspect, systems and methods are disclosed for a virtual reality environment which interfaces to medical treatment apparatus and with medical service providers to share the medical findings and to decrease the discomfort, anxiety and pain of a patient during a procedure, such as radiation therapy, medical imaging (CT, MRI, PET), medical endoscopy procedures (bronchoscopy, colonoscopy, proctoscopy, cystoscopy, etc) or biopsy.

In yet another aspect, systems and methods are disclosed for monitoring a patient by positioning the patient for a predetermined medical mission; sensing biometric and physical conditions of a patient during the mission, and displaying a multimedia interaction with the patient to keep the patient in a predetermined position to improve efficacy of a medical mission.

In a further aspect, the Virtual Reality Medical Application System is a medical system including a combination of hardware and software that will improve a patient's ability to remain still during medical procedures that require a patient to not move. The system includes three components: the hardware component; the software component; and a sensor component. The hardware component consists of a three dimensional (3-D) goggle to provide visual images to patients, noise-cancellation headphone and microphone system to provide 3-way communication between the patient, the healthcare provider, and the Virtual Reality Medical Application System software.

Implementations of the above aspects can include one or more of the following. The medical mission can be an operation, a treatment, a biological sampling, an irradiation process, medical endoscopy, angiography, or a body medical imaging scan. The system can render a visualization with a virtual reality display to interact with the patient or the real image of the findings from the endoscopy. Visual images can be provided to patients with a three dimensional (3-D) goggle. The system can render sound to patients with a noise-cancellation headphone and microphone system to provide a 3-way communication between the patient, a healthcare provider, and a Virtual Reality Medical Application System software.

The system can render a patient specific 3-D game controlled by the patients. The patient-controlled game environment can provide a good distraction to relieve pain and anxiety. A virtual simulation of real life scenery can be provided or the real image or video of the procedure can be shown to the patient. The system can render images of a procedure that a healthcare provider wants to share with the patient.

The sensing can include tracking motion or capturing biofeedback data. The motion tracking uses gyroscope and accelerometer sensors on a 3-D goggle to detect head motion and an array of Inertial Measurement Units (IMU) are used to track the body. IMU's are electrical components utilizing a combination of gyro meters, accelerometers, and magnetometers to track motion in 3 dimensional space. IMUs are placed on various parts of the body to monitor patient body motion. The system can detect one or more of blood pressure, heart rate, EEG, and EKG. The system can include treatment for one of: radiation therapy, brachytherapy, Computed Tomotherapy (CT), Positron Emission Tomotherapy (PET), Magnetic Resonance Imaging (MRI), angiography, biopsy and endoscopy. The virtual reality display relaxes or distracts the patient from anxiety or pain. The system can share clinical information with the patient using the multimedia interaction. The system can guide a patient into a reference position for setup before each treatment. The system can detect a patient position using a 3-D body sensor, comparing the patient position to the reference position, and providing feedback to the patient to move to the reference position. Patients can play a game that negatively reinforces the patient to not move utilizing game play mechanics. Alternatively, the system can provide levels of positive reinforcement to reward the patient for remaining still.

In yet other embodiments, the Virtual Reality Medical Application System of one embodiment utilizes a three-dimensional virtual reality game/simulation and sensors to feed the information directly to the patients to help the patient remain still voluntarily. In a preferred embodiment, the patient will play the game wearing a head mounted display or HMD or Head Mounted Display. The HMD will provide a view into the virtual world where the patient can see himself as an avatar. The HMD will also provide motion tracking of the head and a sensor such as a camera will track the movement of the patient's body. When the patient moves in the real world, his avatar will move in the virtual world. Since, the movement is detected by the game, and the patient will immediately see that he is moving in real time, the game will negatively reinforce the patient to not move utilizing game play mechanics. For example, playing a virtual game of hide and seek, where movement and being detected will make you lose the game. This is one example of negative reinforcement. There is also positive reinforcement in that has the player completes various levels by remaining still, he is positively reinforce with an achievement. As he builds more achievements and levels up, he will want to remain still. The virtual reality provided by the goggles and headphone and microphone will help patients remain relaxed by distracting patients from the stressful environment of the treatment room, hence relieve the anxiety and discomfort or pain.

The Virtual Reality Medical Application System of one embodiment of the invention also utilizes biofeedback data via sensors such as heart rate, blood pressure, body motion, EKG, EMG, and EEG to enhance the game experience, and to improve the treatment efficacy to the patient. For instance, using the hide and seek game as an example outlined above, when the character seeking for the patient (e.g. his or her avatar) is approaching the avatar's hiding place, if the system detects an increase heart rate or increase blood pressure, the system may have the seeking character retreat from the patient's avatar thus reducing the anxiety level of the patient and thus increasing the odds of the patient not moving.

The three-way communication system allows for continuous communication between patient, the healthcare provider, and the simulated game (software).

In an application of the Virtual Reality Medical Application System of one embodiment of the invention associated with a radiation, the radiation treatment typically takes about 20-30 minutes overall. However, during this 20-30 minute treatment, there is a crucial window of about 10 minutes where the patient should be absolutely still. During this treatment period, the Virtual Reality Medical Application System utilizes innovative game play to keep the patient relatively still for 30 minutes but focus on keeping the patient absolutely still for the crucial time period. In the case of radiation therapy, this is ten minutes. During this critical period, the game play may have heightened requirements for remaining still, coupled with increased scoring rates during this critical period, the gamification of the medical process results in a more effective treatment.

Virtual Reality Medical Application System of one embodiment includes a detection-notification cycle which is automated because the patient receives real time feedback to not move. This reduces the complications caused by human error. For instance, because the patient is immersed in the virtual environment, he or she cannot see or hear the external environment, including the rather noisy radiation machine or MRI machine or other medical equipment and environment. This environmental isolation helps the patient relax and increases their ability to remain still during the procedure. Moreover, the patient's immersion in a 3-D world via a HMD has analgesic properties for acute pain, which provides for a reduction in pain perceived by the patient.

Advantages of the above aspects and implementations may include one or more of the following. The apparatus and method decrease the movement of patients undergoing medical procedures such as radiotherapy. The system advantageously provides an apparatus and method to decrease the movement of patients undergoing medical procedures such as radiotherapy which does not use physical restraints or chemical sedatives to immobilize a patient. The apparatus and method decrease the movement of patients undergoing medical procedures such as radiotherapy which is non-invasive and comfortable. The apparatus and method decrease the movement of patients undergoing medical procedures such as radiotherapy which monitors the real-time position of a patient and relays the information to the patient about the specific area of the body and allows patient to make adjustment to get back to the reference or desired position. The apparatus and method decrease the movement of patients undergoing medical procedures such as radiotherapy which alerts a third party (operator or technician) of excessive movement outside a set range and which part of the body. The apparatus and method assure the safely to patients undergoing medical procedures such as radiotherapy which send an interrupt signal instantly to the radiation equipment to pause the radiation beam due to excessive movement outside a set range. The apparatus and method decrease the movement of patients undergoing medical procedures such as radiotherapy which provides a virtual reality system which visualizes the patient's current physical and biometric measurements and allows for the real-time adjustment of their physical and biometric measurements in response.

Yet other advantages may include one or more of the following. The system enables tight control of radiation exposure for children as children are naturally more anxious than adults. Staying still for prolonged periods of times for the treatment is a difficult proposition for children and the use of mechanical stabilization devices or sedatives is commonly used. The mechanical stabilization devices generally cause additional anxiety in children as they are bound and immobilized, resulting in crying, screaming, and minute movements as they struggle to become free. The Virtual Reality Medical Application System provides a virtual reality escape or "games" coupled with EEG and EMG sensors that can relieve patients' chronic pain and depression.

The use of sedatives, although effective to immobilize, comes with medical risk of the sedative medications, costs (up to several thousand dollars per treatment), and extended induction and recovery time (3-5 hours per treatment). This risk is repeated every day, days per week, for period of 3-6 weeks. The system's game and role playing modes allow children patients to be comfortable during radiation treatment sessions in a way that is cost-effective, drug free, restraint free, and fun manner.

Overall, the Virtual Reality Medical Application System of the present invention provides for high levels of patient safety, provides for a patient controlled treatment session, provides non-invasive patient position monitoring using no X-ray scanning, automated patient position management without requiring any operator involvement, and provides for instant communication with a patient during treatment, and provides an overall cost-savings to traditional treatment approaches.

BRIEF DESCRIPTION OF THE DRAWING

The nature, objects, and advantages of the present invention will become more apparent to those skilled in the art after considering the following detailed description in connection with the accompanying drawings, in which like reference numerals designate like parts throughout, and wherein:

FIG. 13 includes an exemplary title page in FIG. 13 including a game name, and representative game graphics to introduce the patient to the game environment;

FIG. 14 is an exemplar of various game avatar characters, such as an eccentric doctor, a dinosaur, and a boy and girl (patient) avatar that can be used in the game of the Virtual Reality Medical Application System of the present invention;

FIG. 15 is an exemplary avatar selection screen in which an eccentric doctor selects a boy or girl (patient) avatar, such as by the patient rotating his or her head in the direction of the desired avatar, such as turning the head right to select the girl avatar, or left to select the boy avatar, with the selection being advanced to the next game screen;

FIG. 16 is an exemplary display of a game within the Virtual Reality Medical Application System of one embodiment of the present invention depicting the patient avatar on a flying skateboard and traveling through a virtual forest in pursuit of lost dinosaur eggs;

FIG. 17 is an exemplary map of a game within the Virtual Reality Medical Application System of one embodiment of the present invention showing a representative forest with colorful topography, and the advancement of the patient avatar from an origin to an end point designed to allow the avatar to gather the stolen eggs from the forest;

FIG. 18 is an exemplary display of the game showing the egg-stealing robot, the dinosaurs, and the patient avatar hiding from the robot in order to avoid detection to protect the dinosaur eggs;

FIG. 19 is an exemplary display of the game showing the patient avatar riding a flying skateboard through the virtual forest environment in search for stolen dinosaur eggs, and providing a patient with a motion status indicator light on the skateboard corresponding to patient movement measurement feedback to the patient, such as green for good, yellow for minimal patient motion detected, and red for too much motion detected, and an exemplary map identifies where the patient avatar is within the virtual forest path;

FIG. 20 is a representative game end screen reporting the patient's success in collecting all of the stolen eggs from the virtual forest;

FIG. 21 is a representative game end screen reporting the patients' failure in collecting all of the stolen eggs from the virtual forest;

FIG. 22 is representative display of the array of IMU for body motion detection;

DETAILED DESCRIPTION OF A PREFERRED EMBODIMENT

Hardware System Description

Figure 1:
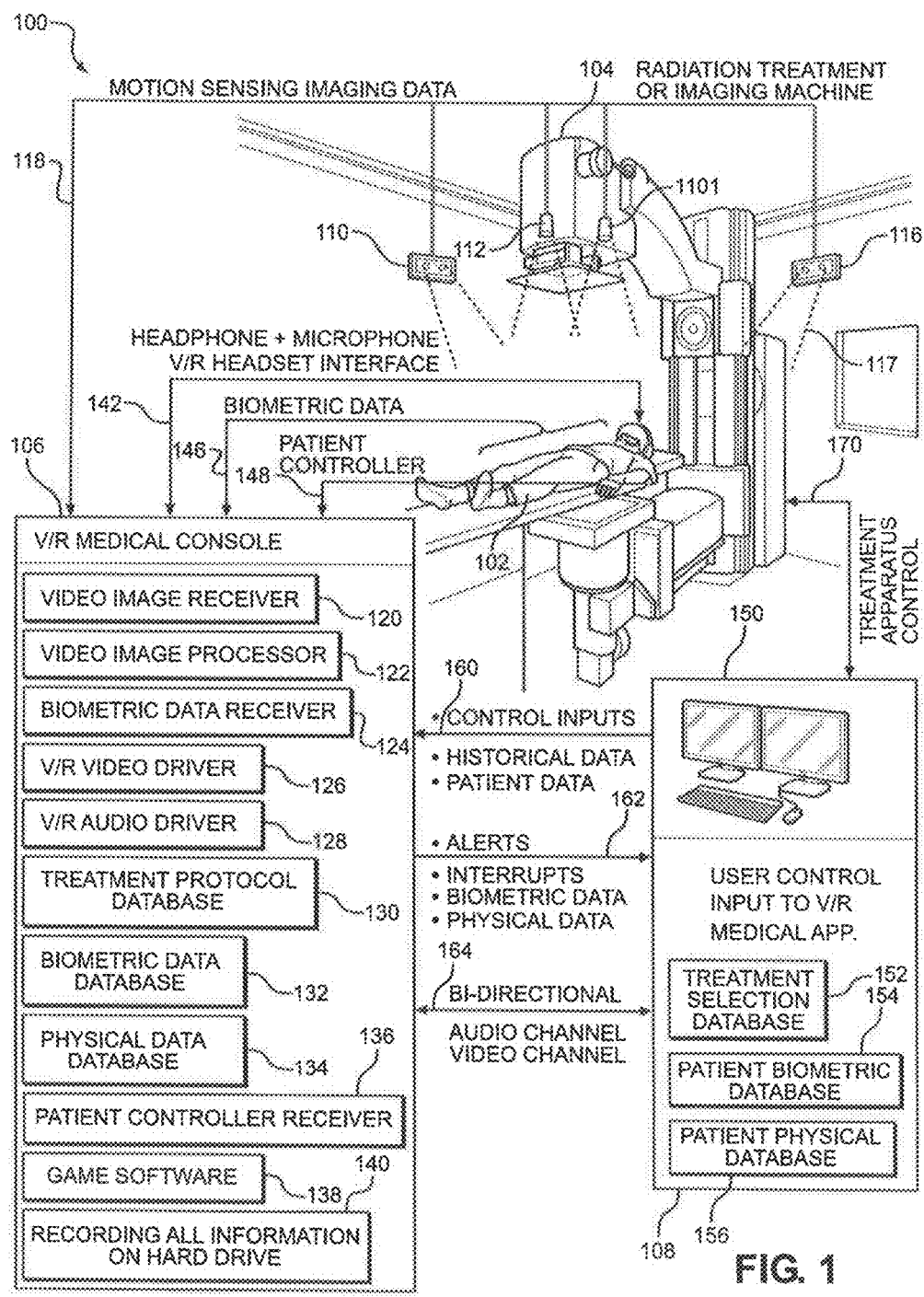
FIG. 1 is a system level diagram of the Virtual Reality Medical Application System of one embodiment of the present invention including a Virtual Reality Console having a video receiver and processor for monitoring patient movement, a biometric receiver and processor for monitoring patient biometric conditions, and patient information and user interface including a virtual reality headset and patient controller, in combination with an array of motion sensors, biometric data collection devices, and a medical treatment apparatus, such as an X-ray radiation treatment device or imaging devices (CT, MRI, PET), having a treatment selection database, patient biometric database, and patient physical database.

Referring initially to FIG. 1, a system level diagram of the Virtual Reality Medical Application System of the present invention is shown and generally designated 100. System 100 is intended to treat a patient 102, and includes a treatment apparatus 104, such as a radiation-delivering X-ray system or medical imaging MRI system. A Virtual Reality Console 106 interfaces to a user, or technician, controller 108 to cooperate with the treatment apparatus 104.

System 100 also includes a number of imaging devices 110, 112, 114, and 116, each having a field of view 117 (shown in dashed lines) to perceive movement of patient 102. Signals from imaging devices 110, 112, 114, and 116 provided data along connection 118 to the video image receiver 120 in VR Medical Console 106, which also includes a video image processor 122 to process the video images to detect patient movement and monitor patient position. A biometric receiver 124 is provided and includes a processor for monitoring patient biometric conditions including the motion sensor for 3-D spatial position. Console 106 also includes a virtual reality video driver 126 and virtual reality audio driver 128.

A treatment protocol database 130, biometric data database 132 and physical data database 134 stores and provide data for patient treatment, and can provide specific patient data from prior treatment sessions, as well as store current treatment data for use later. Also, all treatment data may be stored in hard drive 140.

A patient controller receiver 136 and game software 138 reside in VR medical console 106 to provide the virtual reality experience for patient 102. Console 106 interfaces with the virtual reality headset, headphone and microphone via input 142, and biometric data is provided to console 106 via input 146, and patient controller input is received on input 148.

A VR Medical Application controller 108 includes a treatment selection database 152, a patient biometric database 154 and a patient physical database 156, and may include a computer console 150 for the technician to operate and interface with the Reality Medical Application System of the present invention. Control signals are provided from console 150 to treatment apparatus 104 via channel 170, and may include safety features, such as device interrupts, and error condition notifications.

Data may be exchanged between console 106 and user controller 108. For instance, control inputs 160 including historical data and patient data, alerts 162 including interrupts, biometric data and physical data, and bidirectional channel 164 including audio and video signals. These data channels provide a technician seated apart from the patient the ability to fully monitor the patient 102, and the patient's interaction with the Virtual Reality Medical Application System and the treatment apparatus 104.

Radiation from treatment apparatus 104 causes cellular degradation due to damage to DNA and other key molecular structures within the cells in various tissues. It was discovered that with controlled amounts of radiation, the effects caused by radiation can be utilized to treat certain diseases such as cancer. With the use of radiation, several previously untreatable diseases have been able to be successfully treated using radiation therapies. However, along with the curative effects of radiation are negative side effects. The prolonged unnecessary exposure to radiation to normal organs includes both immediate and delayed side effects. The immediate side effects of radiation exposure include nausea and vomiting, diarrhea, pain, headaches, and skin or organ burns, whereas the delayed effects could include fatigue, weakness, hemorrhaging, leukopenia, epilation, paralysis, brain damage, blindness, perforation, ulceration, malabsorption, organ failure, and other various side effects. Additionally, the prolonged overexposure of unnecessary radiation may cause more serious complications and may lead to mortality. The system of FIG. 1 reduces the serious side effects of utilizing radiation as a form of medical treatment, and limit the exposure of radiation to healthy tissue by focusing the radiation solely on the diseased tissue by training patients to remain still so that the radiation can be focused on diseased portions, and minimizing the radiation exposure to the uninvolved healthy organs.

The Virtual Reality Medical Application System of one embodiment of the invention is suitable for a variety of medical applications. For instance, all patients of all ages that receive radiation therapy (including brachytherapy) will have an improved experience using the present invention. There are about 700,000-800,000 patients that receive radiation treatments yearly, and many of these patients are unable to remain still due to pain or anxiety, and which will benefit an improvement in their treatment from the present invention.

The Virtual Reality Medical Application System of one embodiment also provides benefits when used with respiratory-gating/tracking of a tumor during radiation therapy. While a patient is receiving radiation treatment for the duration of about 10-15 minutes, there is tumor motion due to respiration, particularly tumors in the lung, breast, and liver. The normal radiation field or treatment portal has to be enlarged to account for this tumor motion, which means more normal structure tissues is being exposed the radiation treatment, hence more treatment side effects. One way to reduce the size of treatment portal or radiation field size is to turn the radiation on only during part of the respiration cycle by having holding their breath for a period of 20-60 seconds. This process is called "respiration gating". With the input from body motion sensor, the present invention facilitates the accurate timing of the radiation beam ("respiration gating") with the respiratory cycle to minimize the effect of tumor motion. The body sensor will send feedback to patients via the headset goggle to instruct patients to hold their breath at the right movement or similar 3-D chest position and send signal to the treatment machine and/or operator to allow the radiation beam to turn on.

The Virtual Reality Medical Application System of one embodiment also provides benefits to patients using the body sensors and goggle feedback is non-invasive, more objective, easy compliance, patient-controlled, and less expensive system. This system also provides additional sensory input to patients and operators such as 3-D body spatial position, oxygen saturation level, heart rate, body temperature, etc.

The software component provides a variety of patient specific 3-D games that are controlled by patients, virtual simulation of real life scenery (car racing, hot-air balloon, fish-eye view, etc), and may include real time images of the procedure that a healthcare provider wants to share with patient, such as an inside image of the colon from the colonoscopy. The proposed system can be used to decrease the discomfort, anxiety and pain patients during procedures, such as, medical imaging (CT, MRI, PET), medical endoscopy procedures (bronchoscopy, colonoscopy, proctoscopy, cystoscopy, etc) or biopsy.

The 3-D games and virtual simulation software will be developed is, in a preferred embodiment, run on Linux, and the technician console is a cross platform and runs on Microsoft Windows, Apple Mac OS, and Linux in a custom medical-grade computer with input/output ports and storage system.

The sensor component performs two major functions: motion tracking and biofeedback. For motion tracking of the patients, the head and body are tracked separately. The tracking of the head and the body both utilize sensors based on Inertial Measurement Units (IMU). IMU's are electrical components utilizing a combination of gyro meters, accelerometers, and magnetometers to track motion in 3 dimensional space. For the head, the IMU's are built into the 3-D goggles. For the body, 3D motion is tracked via an array of IMUs that are placed on the various joints of the body. The array of IMUs transmit data to a central hub and then sent to the Virtual Reality Medical Application System. For biofeedback, sensors such as blood pressure, heart rate, EEG, and EKG, among others will help a technician keep informed of the patient condition, and will tend to determine the game play mechanics.

Alternatively, motion may be detected using a video based motion sensing device, capable of three-dimensional motion detection. One such sensor is commercially available as the Kinect sensor. Kinect builds on software technology developed internally by Rare, a subsidiary of Microsoft Game Studios owned by Microsoft, and on range camera technology by Israeli developer PrimeSense, which developed a system that can interpret specific gestures, making completely hands-free control of electronic devices possible by using an infrared projector and camera and a special microchip to track the movement of objects and individuals in three dimensions. This 3D scanner system, often called Light Coding, employs a variant of image-based 3D reconstruction.

The Kinect sensor is a horizontal bar connected to a small base with a motorized pivot and is designed to be positioned lengthwise above or below the video display. The device features an "RGB camera, depth sensor and multi-array microphone running proprietary software" which provide full-body 3D motion capture, facial recognition and voice recognition capabilities. Kinect sensor's microphone array enables its attached devices, such as an Xbox 360, to conduct acoustic source localization and ambient noise suppression, allowing for things such as headset-free party chat over Xbox Live.

The depth sensor consists of an infrared laser projector combined with a monochrome CMOS sensor, which captures video data in 3D under any ambient light conditions. The sensing range of the depth sensor is adjustable, and Kinect software is capable of automatically calibrating the sensor based on gameplay and the player's physical environment, accommodating for the presence of furniture or other obstacles.

The Virtual Reality Medical Application System of the present, in a preferred embodiment, is particularly suited for use with patients undergoing radiation therapy, but may be used to cover patients undergoing brachytherapy, Computed Tomography (CT), PET, Magnetic Resonance Imaging (MRI), angiography, biopsy procedures and endoscopy such as bronchoscopy or colonoscopy, for example. In addition to keeping the technician informed of the status of the patient, the Virtual Reality Medical Application System of one embodiment of the invention also helps the patient relax and also distract from the anxiety and pain of these procedures. The visual and audio system allows the healthcare provider to share the clinical information to the patient (e.g., the images of abnormal findings from the colonoscopy) The Virtual Reality Medical Application System of one embodiment of the invention also provides benefits in for patient setup before each radiation treatment. When patient comes in every day for the radiation treatment, he/she must be positioned in exactly the same position as the reference or planned position. This is performed by using restrained devices, adjustment by operators/technicians, and then verified by using invasive X-ray images or Computed Tomography (CT scan). All of these add times (5-10 minutes), cost (hundred of dollars), and unnecessary radiation exposure to patients. The Virtual Reality Medical Application System of one embodiment of the invention uses body sensor to detect the 3-D body position, comparing to the reference or desired position, and give feedback to patients via a game avatar to instruct patient to make adjustment on a specific body parts on their own to get within the reference position. Therefore, it provides a much less expensive, noninvasive (no radiation imaging required), more accurate, and time-efficient. The benefit of IMU based motion tracking over video based motion (kinect) tracking is IMU based motion tracking does not require a patient's skin to be exposed so that treatment can be done while the patient is covered. With video based motion capture, the body needs to be exposed, which could be uncomfortable for patients with certain area such as breast and pelvic regions.

The Virtual Reality Medical Application System relies on motion sensors, goggle, and 3-D game to monitor patients during the radiation treatment and provide instant feedback to patients to remind them staying still via such process as pausing of the game, commands from game character, etc. Since radiation treatment is typically delivered in 15-30 min during which patients must remain still, any unnecessary involuntarily movement will cause radiation to deliver incorrectly to normal structures and missing tumor. Within radiation therapy, the Virtual Reality Medical Application System of one embodiment of the invention is particularly well suited for use with children with cancer that undergo radiation therapy. There are about 10,000 cases of children cancer in the U.S. every year, and about ½ of these children will undergo radiation therapy daily for several weeks.

Because, kids typically can be very anxious, staying still is a significant problem during these procedures. The alternative to keeping still voluntarily is to sedate them via intravenous sedatives and anesthetic gas. Sedation comes with anesthesia medication risk, costs several thousand dollars per day, and extends daily treatment time from less than an hour to more than 4 hours per day. The Virtual Reality Medical Application System of the present will be useful because it will reduce the complications that can come from sedating a child, reduce costs since sedation will not be necessary, and speed up the procedure since there is no need to wait for the anesthesia and its recovery.

The Virtual Reality Medical Application System of one embodiment also helps patients that undergo medical imaging (MRI, CT, and PET) that are too anxious, such as due to claustrophobia, to remain calm. There are estimated 30 million of patients receiving MRI yearly, and about 5% of these patients have claustrophobia that requires sedation with medication. The Virtual Reality Medical Application System of one embodiment is also useful for patients undergoing minor procedures such as biopsy, angiography, colonoscopy, endoscopy, bronchoscopy, dental surgery, cosmetic surgeries, interventional radiology procedures, etc. The Virtual Reality Medical Application System of one embodiment of the invention provides distraction, or escape, from the procedure, thus reducing the need for sedatives and pain medication. The visual and audio system allows the healthcare provider to share the clinical information to the patient (e.g., the images of abnormal findings from the colonoscopy and share informed consent on what to do with certain findings). The Virtual Reality Medical Application System of one embodiment can also allow patients to visualize the real live images of the procedure that the physicians see on their scope. Since the patients are not sedated, their physicians can communicate and get patients' consent to certain procedures such as decision to biopsy or removal. This is particularly beneficial when the lack of patient consent would prohibit a physician from performing a procedure that would be routine, but were unanticipated at the start of the procedure. Moreover, such active patient participating would eliminate countless repeat medical procedures.

Another use of the Virtual Reality Medical Application System of one embodiment of the invention includes psychotherapy for patients that are receiving chemotherapy. These patients typically spend 4-8 hours per day in the chemo-infusion rooms or in the hospital receiving their chemotherapy drugs intravenously. The effect of chemotherapy drugs to the brain and exposing to the environment can affect patients' cognitive functions (memory, fluency, attention, motor coordination) and cause depression, anxiety, hopelessness. This condition is sometime called "chemo-brain". The Virtual Reality Medical Application System provides virtual reality escape or "cancer fighting games" that can relieve patients' stress, anxiety, and other cancer related symptoms from chemo-brain effects.

Also, the Virtual Reality Medical Application System of one embodiment is suitable for psychotherapy for patients that have acute pains such as those just have surgery, trauma, such as accidents or burns. The Virtual Reality Medical Application System provides a virtual reality escape or "games" that can relieve patients' stress, anxiety, and other related symptoms, as well as provide psychotherapy for patients that have chronic pain, depression, anxiety disorder, or other personality/mood/affect disorders (autism, OCD, etc. . . . ) Also, the Virtual Reality Medical Application System of one embodiment of the invention is suitable for psychotherapy for patients that suffer pain from missing arms or legs ("phantom limb pain"). There are approximately 70,000 patients in the U.S. who lose their arms/legs due to military combat or disease such as diabetic or cancer. These patients suffer chronic pain and depression due to the missing limbs. The Virtual Reality Medical Application System provides a virtual reality escape or "games" coupled with body motion sensors, EEG and EMG sensors that can relieve patients' chronic pain and depression.

Overall, the Virtual Reality Medical Application System of one embodiment provides for high levels of patient safety, provides for a patient controlled treatment session, provides non-invasive patient position monitoring using no X-ray scanning, automated patient position management without requiring any operator involvement, and provides for instant communication with a patient during treatment, and provides an overall cost-savings to traditional treatment approaches. Moreover, this "patient control" experience, as compared to other systems where patient is "passive", provides an overall improvement to the patient experience, and allows for the real-time sharing of information and communication with the patient. This provides a more efficient procedure, particularly when a procedure requires the need to obtain patient consent during treatment, which is problematic and time-consuming when the patient is under anesthesia.

Figure 2:
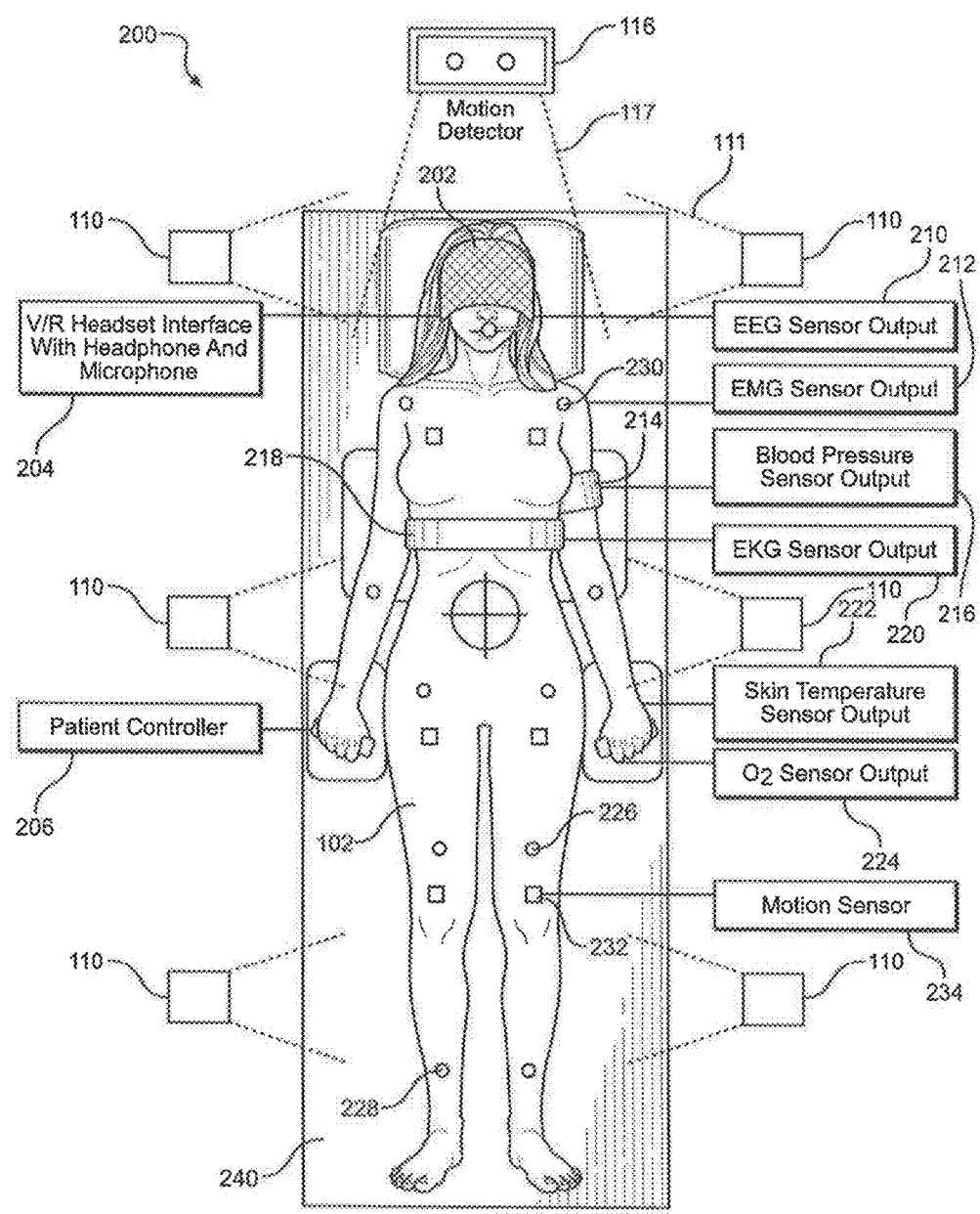
FIG. 2 is a top plan view of an exemplary patient positioned flat on her back on a treatment table of FIG. 1, and having a number of biometric sensing devices positioned to sense a variety of biometric signal levels, a virtual reality headset with headphone and microphone, one or more patient controllers to receive patient input, a number of imaging cameras positioned to detect patient movement, and a number of position locator tags distributed on the patient's body for precise position detection, and a representative radiation target on her abdomen indicating the location of the radiation treatment or medical procedure to be performed.

Referring to FIG. 2, a top plan view shows an exemplary patient 102 positioned flat on her back on a treatment table 240 of FIG. 1. Motion detectors 110 having a field of view 111, and motion detector 116 having a field of view 117 monitor the patient's position. A virtual reality head mounted display (HMD) 202 is positioned over the patient's eyes, and provides a visual interface for the patient to see during treatments. A Virtual reality headset interface having a headphone and microphone 204 receives and transmits signals from the HMD 202 to VR medical console 106 along interface 142 (shown in FIG. 1).

FIG. 2 also shows a number of biometric sensing devices positioned to sense a variety of biometric signal levels. For instance, an EEG sensor output 210, EMG sensor output 212, blood pressure sensor 214 provides data to blood pressure sensor output 216, EKG sensor 218 provides an EKG sensor output 220, skin temperature sensor output 222, and oxygen sensor output 224 are channeled to VR medical console 106 as shown in FIG. 1.

Also, a number of motion sensors 232 may be positioned on patient 102 to provide mechanical measurement of the patient during treatment, and may include a number of different measurement techniques including gyroscopes, strain gauges, Hall-effect sensors, and other techniques known in the art. The signals from the mechanical measurement devices are provided to motion sensor output 234 for routing to VR medical console 106.

In addition to video imaging devices 116 and 110, and mechanical motion sensing devices 232, a number of position locator tags, or reference markers, 226, 228 and 230 may be positioned on the patient. These markers may have wavelength-specific reflection properties (such as infrared or ultraviolet), enabling an imaging system to very specific focus on the patient position using the markers, and comparing those marker positions to known references positions.

In one embodiment of the present invention, motion sensors 116 may be of the type utilized in the Kinect2 system. Incorporation of such as system provides several benefits: (a) It is infrared laser projector and a 3-D camera to capture the 3-D body surface; (b) It enables facial recognition; and (c) It enables voice recognition. The (b) and (c) features are very important for patient safety to correctly identifying the correct patient being treated. This is particularly advantageous in critical health care treatment where 130,000 medical mistakes occur annually in which patients receive the wrong surgery or radiation treatment.

A representative radiation target may be placed on the patient abdomen to indicate the location of the radiation treatment, or this target may be optically generated by the treatment device, such as a radiation emitter.

Figure 3:
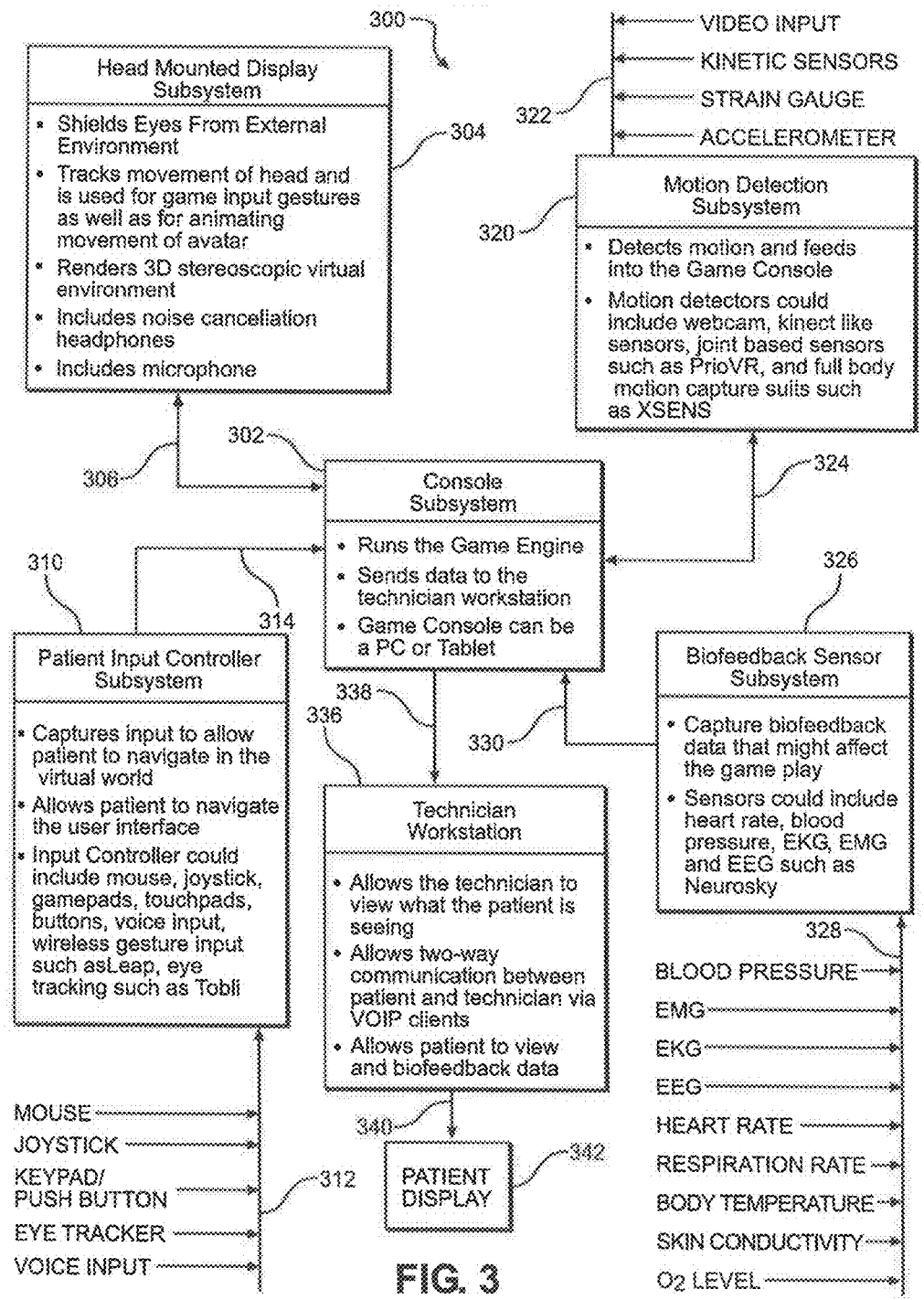
FIG. 3 is a system level block diagram of the hardware of the Virtual Reality Medical Application System of one embodiment of the present invention showing the console sub-system in communication with the virtual reality head mounted display (HMD), the patient input controller sub-system having a variety of user input devices to capture patient input and responses, the patient motion detection subsystem having a variety of motion sensor inputs to detect patient motion, the biofeedback sensor subsystem having a variety of biometric sensor inputs to maintain measurement of critical patient biometric data, and the technician's workstation to provide real-time data to a treatment technician.

Referring now to FIG. 3, a system level block diagram of the hardware of the Virtual Reality Medical Application System of the present invention is shown and generally designated 300. System 300 includes a control subsystem 302 which runs the game engine, sends data to the technician workstation, and incorporates a game console on a personal computer or tablet computer.

Console sub-system 302 is in communication via channel 306 with the virtual reality head mounted display (HMD) 304 which shields the patients eyes from the external environment, tracks movement of the patient's head and is used during game play, and provides the three dimensional stereoscopic display for the patient's virtual environment. In a preferred embodiment of the HMD 304, noise cancelling headphones may be incorporated to provide a sound-proof environment for the patient, and may include a microphone for bi-directional communication with the technician at the console 108.

A patient input controller 310 captures patient input to allow the patient to navigate in the virtual world, and allows the patient to utilize and navigate through the user interface. In a preferred embodiment, the patient input controller can include one or more of eye movement sensors, a mouse, joystick, gamepad, touchpad, button, voice input, and gesture input; with such input signals received on input 312.

A motion detection subsystem 320 detects the patient motion from motion input devices, such as a video input, kinetic sensors, strain gauges, IMs motion sensors and accelerometers on signal line 322, and provides the motion-related data to the game software 138 running in the console 106, and can also provide data to the technician workstation 108. These motion sensing devices provide highly accurate patient position and motion data to motion detection subsystem 320 which in turn communicates this data to console subsystem 302 using interface 324.

Biofeedback sensor subsystem 326 is in communication with a variety of biometric monitoring devices, such as blood pressure monitors, EMG, EKG, EEG, heart rate, respiration rate, body temperature, skin conductivity, and oxygen level monitors along input channel 328. These data measurements may be returned to the console subsystem 302 via channel 330.

The constant measurement of critical patient biometric data provides the Virtual Reality Medical Application System of the present invention to accurately monitor the physical and mental condition of the patient before, during, and after a treatment. These measured biometric signals allow a technician or health care provider to determine in real-time the level of pain and anxiety the patient is experiencing, and thus allows for near real-time adjustment to the treatment. Further this measured patient condition provides the Virtual Reality Medical Application System of the present invention the unique ability to adjust the virtual reality environment to provide the patient with an increased or decreased level of interaction to make the treatment more successful, and the patient experience more positive.

The technician's workstation 336 allows the technician or health care provider to view that a patient is seeing, and may also provide for a bidirectional communication link between the technician and the patient. Also, the technician workstation 336 may allow a patient to view certain procedure-specific data, such as images from a surgical biopsy, colonoscopy, etc. thus facilitating real-time consent from a patient during a procedure. This is of a particular benefit when the inability to secure consent from a patient during a procedure could result in a procedure being terminated prematurely, repeat procedure, or redundant procedures to accomplish tasks that could have been easily completed were consent available. Technician workstation 336 may also provide real-time data to a treatment technician via channel 340 to a patient display 342.

Software System Description

Figure 4:
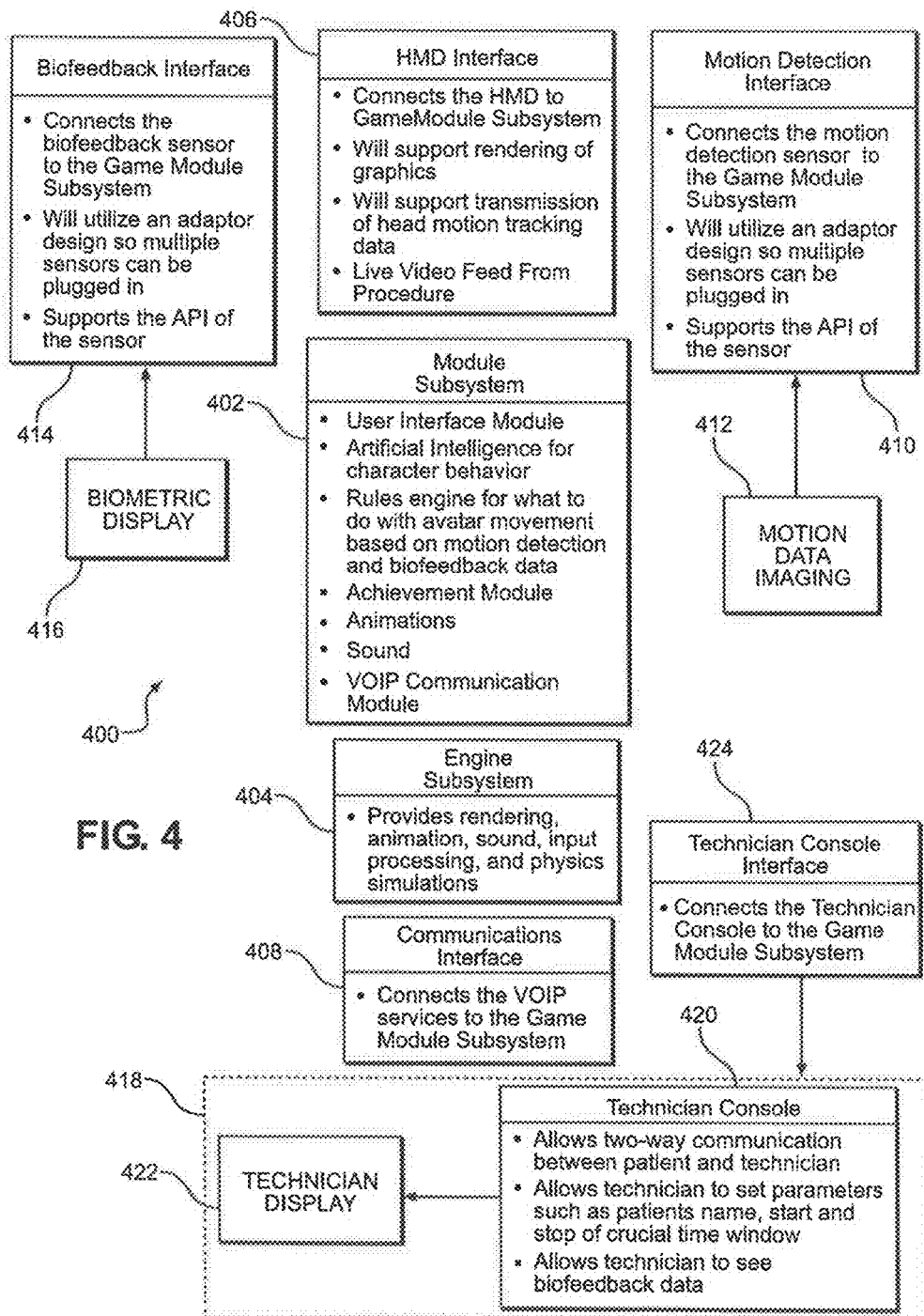
FIG. 4 is a system level block diagram of the software of the Virtual Reality Medical Application System of one embodiment of the present invention showing a module subsystem for the user interface and character behavior to be used in game animations and patient feedback, an engine subsystem that provides patient feedback animations, renderings, and motion simulations, and an associated HMD interface that connects to a game module subsystem and provides graphics and patient head motion tracking and live video to the patient related to the video procedure, a communication interface which interconnects the various modules, a motion detection interface receiving motion data from multiple motion detection imagers and devices, and a biofeedback interface receiving biometric data from the various patient sensors, all in communication with a technician console interface and related technician console.

FIG. 4 is a system level block diagram of the software of the Virtual Reality Medical Application System of the present invention generally designated 400. Software block diagram 400 includes a module subsystem 402 which includes the user interface module, artificial intelligence used for character behavior, a rules engine for determining avatar movement, an achievement module used to track avatar actions, and various animations, sound and communication functions. Engine subsystem 404 provides rendering, animation, sound, input processing and physics simulations to provide accurate virtual reality images and physical behavior.

A head mounted display (HMD) interface 406 interfaces the display to the game module subsystem, and supports the rendering of the graphics in the patient worn virtual reality display. Also, the HMD interface 406 provides motion sensing data back to the motion detection interface 410, as well as may provide the patient with a live video feed from the treatment procedure, facilitating information sharing or consent as mentioned above. To facilitate this communication, communication interface 408 interconnects various modules and VOIP services to the game module system 402.

Motion detection interface 410 receives motion data from various imaging sources 412 and connects the motion detection sensors to the game module subsystem. In a preferred embodiment, module 410 utilizes an adaptor design to accept multiple sensors that can simultaneously or cooperatively monitor the patient position and movement.

Biometric interface 414 connects the various biofeedback sensor inputs to the game module subsystem 402, and utilizes an adapter designed so that the various biometric sensors may be selectively or simultaneously monitored, and can receive information from a biometric data display 416.

A technician station 418 includes a technician console 420 and a technician display 422 that allows bidirectional communication between the technician and the patient, and allows the technician to set motion and treatment parameters and monitor those parameters during the treatment period, and also allows the technician to monitor the patient biofeedback data. The technician station 418 is in communication with the game module subsystem 402 via technician console interface 424.

Operation of the Invention

Figure 5:
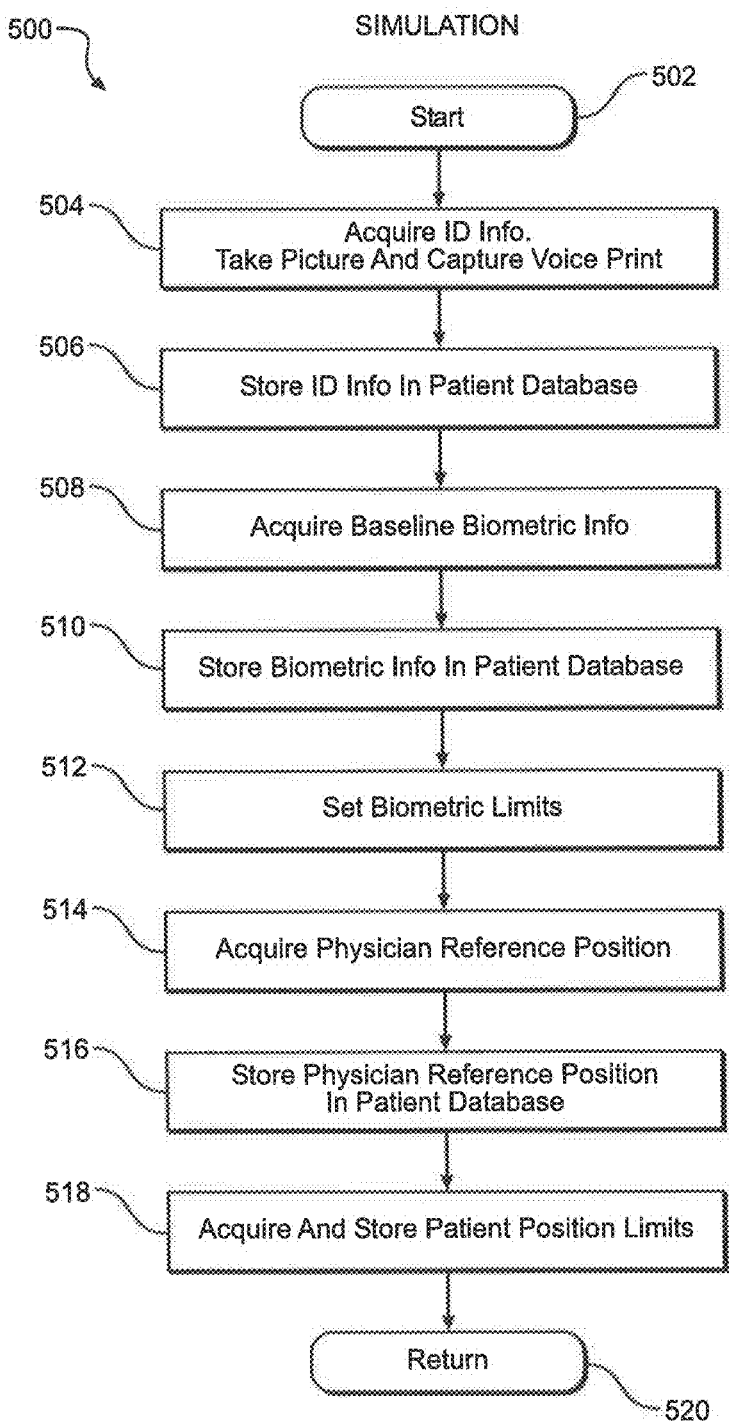
FIG. 5 is an exemplary flow chart depicting the pre-treatment simulation of the treatment using one embodiment of the Virtual Reality Medical Application System of the present invention, including acquiring patient identification data, establishing baseline biometric and position data to be used in subsequent treatments.

FIG. 5 is an exemplary flow chart, generally designated 500, and depicting the method of the pre-treatment simulation of the treatment using the Virtual Reality Medical Application System of the present invention. Method 500 starts in step 502, and begins with the acquisition of patient identification data, including the photograph of the patient and sampling of voice data in step 504. In step 506, this patient identification data is stored in the patient database.

The physician will decide if biometric sensors will be used and if so, which ones will be used, also the allowable deviations from sensors. In step 508, the patient's baseline biometric data is acquired, such as the skin conductivity, EKG, EEG, heart rate, respiration rate, body temperature and oxygen saturation. Once the baseline biometric data is acquired, it is stored in step 510 in the patient database for later retrieval. Additionally, limits on the biometric data, such as normal ranges and range limitations for detecting unsafe conditions, is determined in step 512.

In addition to the biometric baseline data, a patient's physical positioning data is acquired in step 514. In treatments where patient position is critical, the treating physician has the opportunity to accurately and precisely position the patient for his or her treatment in the simulation environment thus making certain that the position of the patient is optimum for the best treatment outcome possible.

A typical simulation would occur one or two weeks before the radiation treatment, and would include the patient undergoing a treatment planning process. During this simulation, the physician will decide on a certain treatment position (called, "reference position") and at that time, a CT (Computed Tomography) is done (sometimes with MRI and/or PET) to plan the radiation treatment (# of beam and directions, # of treatments, outlining the tumor, etc.).

Once this optimum reference position is achieved, the patient position data is stored in step 516 for later retrieval. Following the successful positioning during the simulation, the patient positional limitations are determined and stored in step 518. This provides for position limit setting based on the particular treatment to be performed. For instance, in treatments to the abdomen, such as radiation of cervix or ovarian cancer, the precise position of the lower abdomen is critical, whereas the position of the patient's foot is less critical. In such circumstances, the positional limitations on the abdominal position may be very small, but the positional limitations on the patient's foot may be relaxed.

Once all data from the simulation has been gathered and stored, method 500 returns to its calling procedure in step 520.

Figure 6:
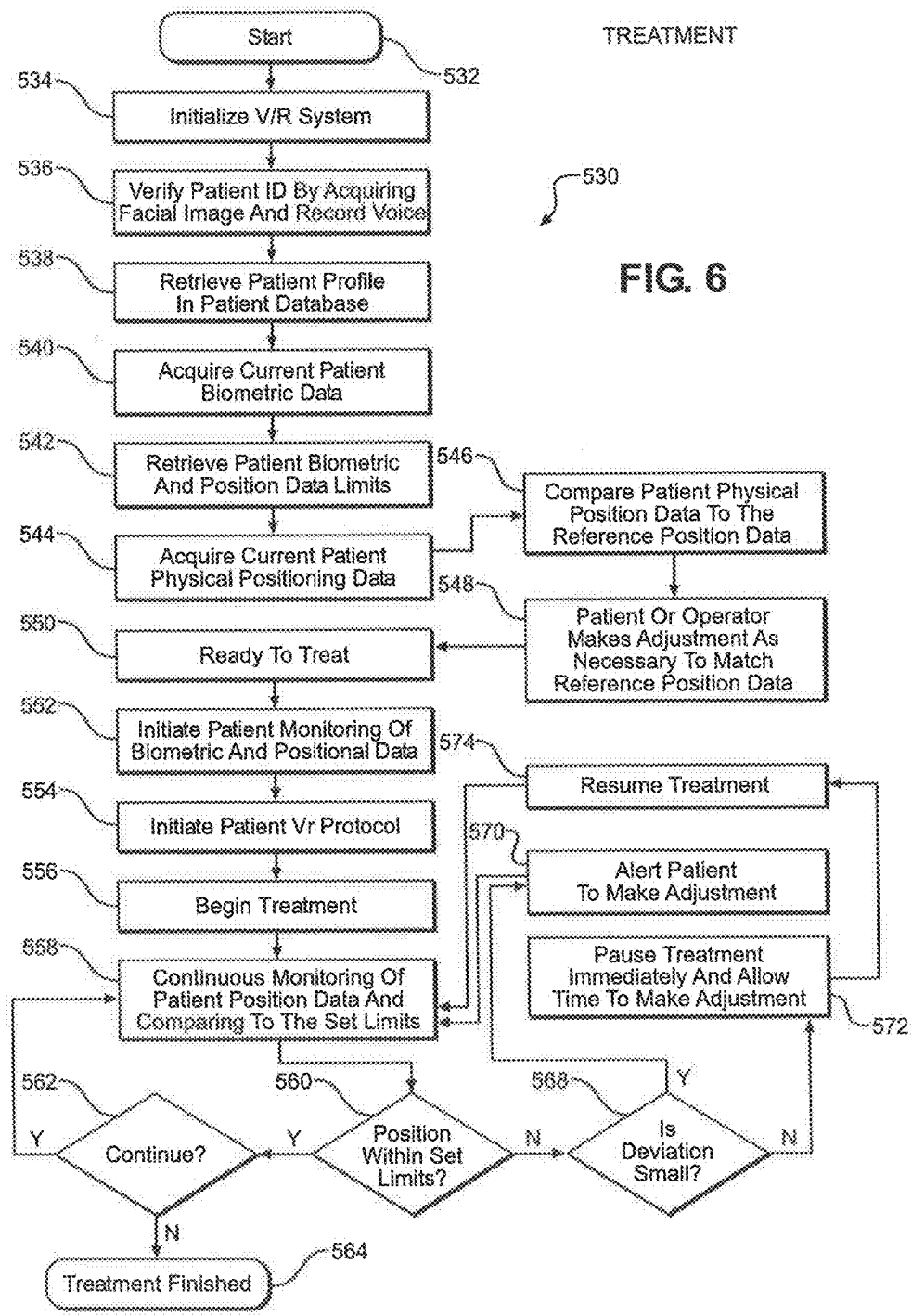
FIG. 6 is a flow chart representing an exemplary operation of the Virtual Reality Medical Application System of one embodiment of the present invention including the preliminary steps executed prior to beginning treatment, including initializing the virtual reality system, customizing the system for the particular patient with current biometric and physical data, establishing data limits, and initiating the patient's virtual reality treatment protocol.

FIG. 6 is a flow chart generally designated 530 and representing an exemplary operation of the Virtual Reality Medical Application System of the present invention 100. Method 530 includes the preliminary steps executed prior to beginning treatment, begins in start step 532 and includes initializing the virtual reality system in step 534. Once the patient identification is verified by acquiring facial image and voice data in step 536, the patient profile is retrieved from the patient database in step 538. The patient's current biometric data is acquired in step 540, and the patient biometric and positional limits are retrieved in step 543.

Prior to treatment initiating, the patient's current positional data is acquired in step 544, and compared to the previously stored reference position data in step 546. If necessary, the patient or operator makes an adjustment to the patient's position to match the reference position data in step 548.

Once positions are matched, the patient is ready to start treatment in step 550. Once ready, the patient biometric and positional data is monitored starting in step 552, and the patient's virtual reality protocol is started in step 554. Once fully immersed in the virtual reality environment, the treatment of the patient begins in step 556.

The patient's positional data is measured in step 558 and compared to the set limitations. If the patient's position is within the set limits as determined in step 560, the treatment is not completed, as determined in step 562, flow chart 530 returns to step 558 for continued monitoring. If the treatment is completed as determined in step 562, the treatment ends in step 564.

If the patient position is not within the set limits as determined in step 560, the magnitude of the deviation is determined in step 568. If the deviation is small, the patient is alerted to make an adjustment in step 570, and control returns to step 558 for continued monitoring and treatment. However, if the deviation is not small, then the treatment is paused in step 572 until the patient makes a proper position adjustment, and treatment resumes in step 574 and control returns to step 558 for continued monitoring and treatment.

Figure 7:
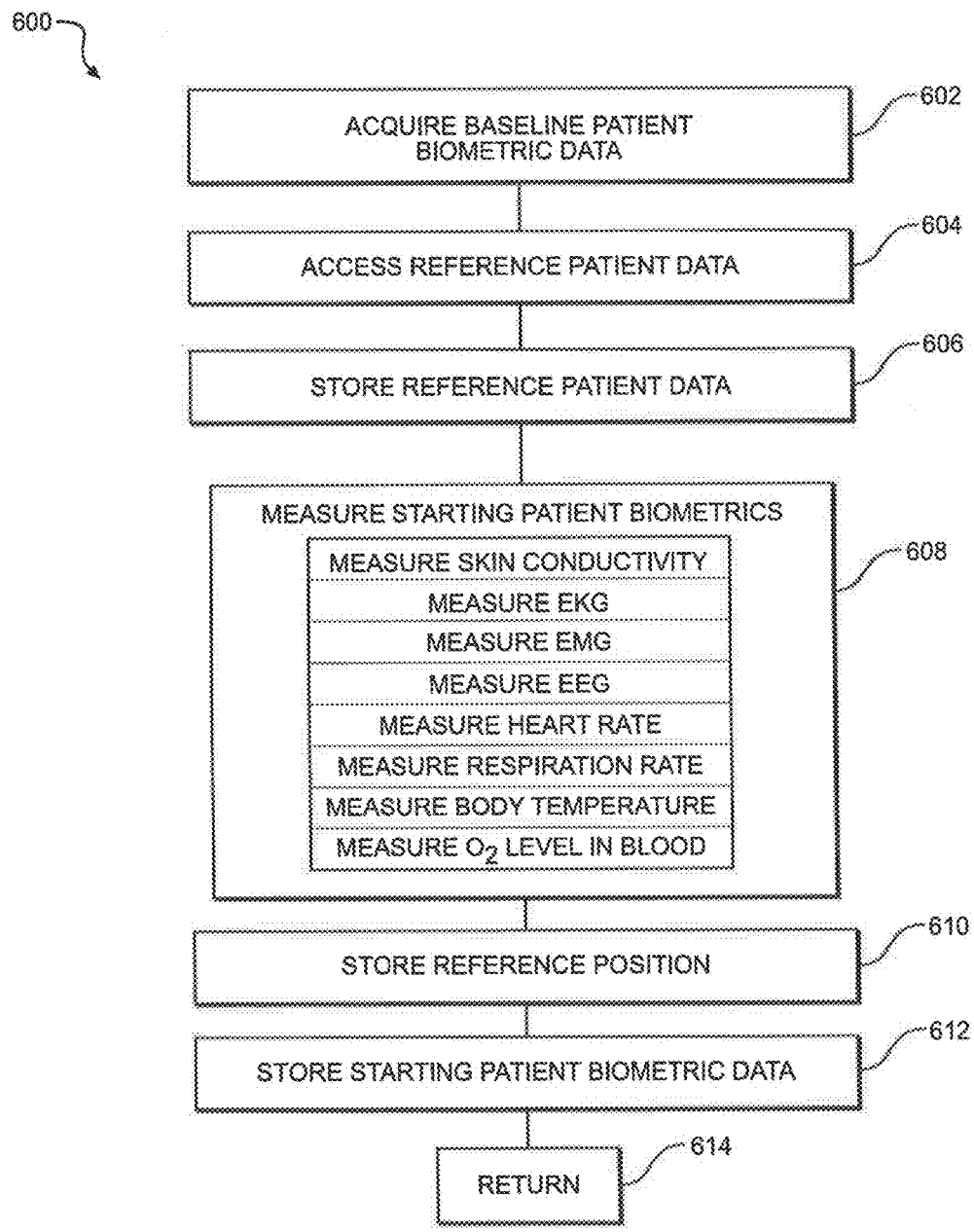
FIG. 7 is a flow chart representing the steps for the acquisition of baseline patient biometric data of FIG. 5, and including the accessing of the patient's historical data, and measuring and storing all patient biometric data, such as 3-D spatial positioning, skin conductivity, EKG, EEG, heart rate, respiration rate, body temperature and oxygen saturation, for example.

Referring now to FIG. 7, a flow chart representing the steps for the acquisition of baseline patient biometric data of FIG. 5 is shown and generally designated 600. Flow chart 600 begins with the acquisition of baseline patient biometric data in step 602. The reference patient data is accessed in step 604, and that data is stored locally in step 606.

The patient's starting biometrics are measured in step 608, and may include the measurement of 3-D body position, skin conductivity, EKG, EMG, EEG, heart rate, respiration rate, body temperature and oxygen level in the blood, and any other biometric data which may be useful for the procedure being performed.

The patient's reference position is stored in step 610, and the patient starting biometric data is stored in step 612. Once complete, the control returns in step 614 to the calling procedure.

Figure 8:
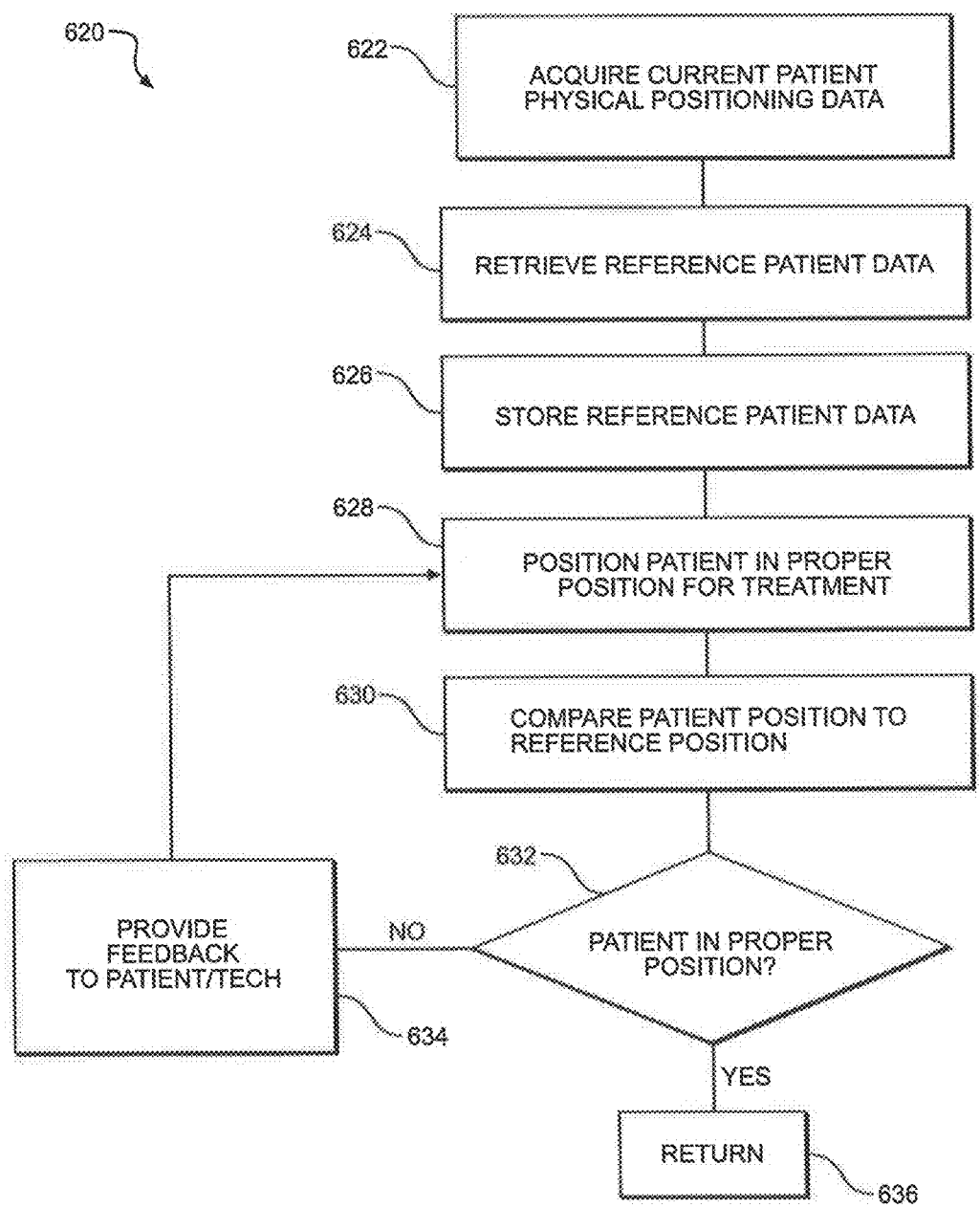
FIG. 8 is a flow chart representing the steps for the acquisition of baseline physical positioning data of FIG. 6, and including the accessing of the patient's historical data and measuring and storing all patient physical data, and then comparing a patient's current position to his baseline data, and providing feedback to the patient to adjust his position to match the baseline data.

Referring to FIG. 8, a flow chart representing the steps for the acquisition of baseline physical positioning data of FIG. 6 is generally designated 620. Method 620 begins with the acquisition of current patient physical positioning data in step 622. The patient reference data is retrieved in step 624, and the reference data is stored locally in step 626.

The patient is positioned in his or her proper reference position in step 630, and verified in step 632. If the patient is not in the proper reference position, feedback is provided to the patient and technician in step 634, and the patient position is then verified in step 628. Once proper positioning is achieved as determined in step 632, control returns in step 636 to the calling procedure.

Figure 9:
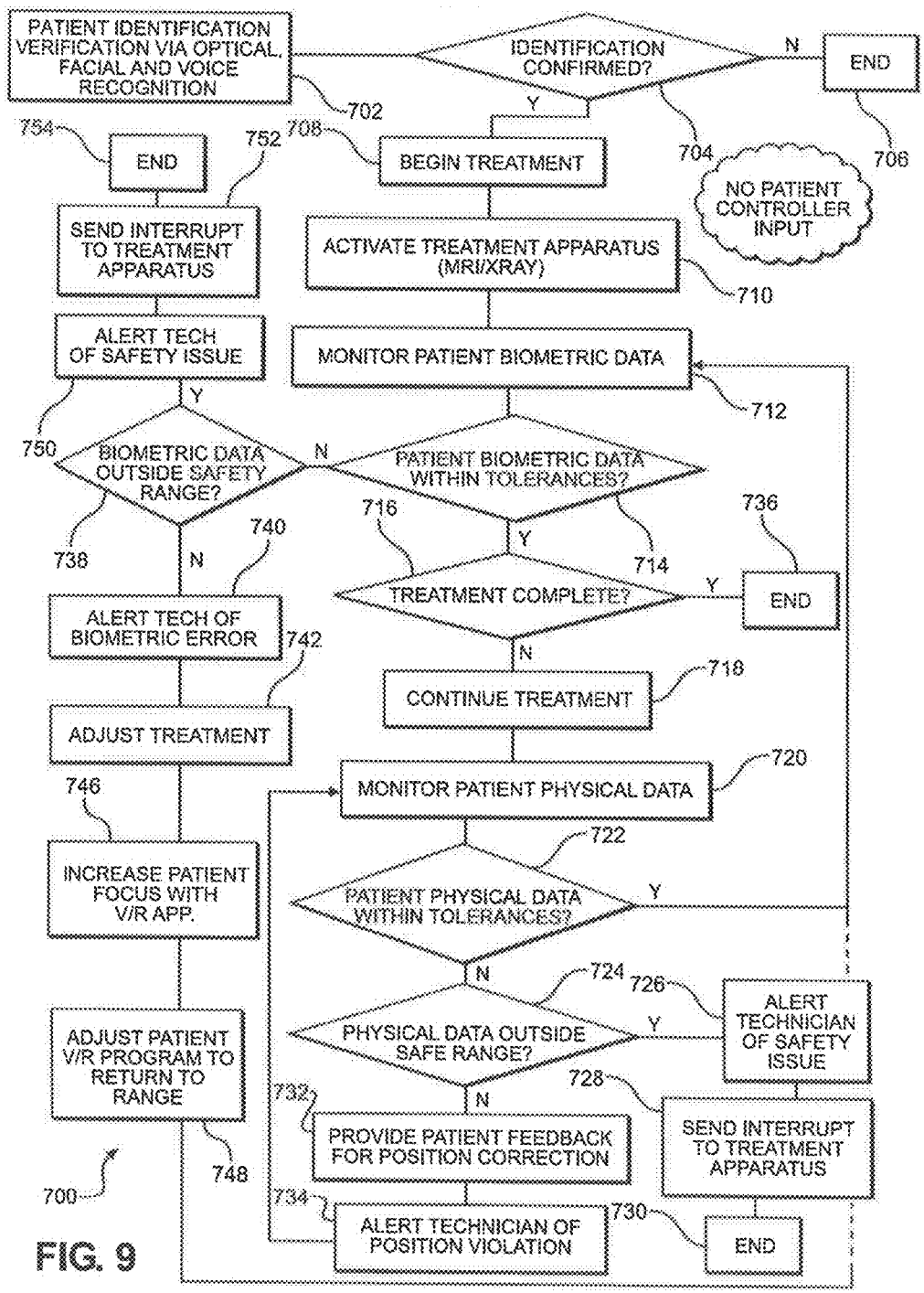
FIG. 9 is a flow chart representing the beginning of treatment of FIG. 6 without using patient controller input, and includes the verification of patient identity, the activation of the medical treatment apparatus, and the subsequent monitoring and evaluation of position and biometric data for compliance and safety, and providing a patient with biometric and positional feedback to assist with correction, and modification of the virtual reality program to facilitate such patient correction.

FIG. 9 is an exemplary flow chart, generally designated 700, and representing the beginning of treatment of FIG. 6 without using patient controller input. Method 700 begins in step 702 with patient identification verification using optical, facial and voice recognition. If identity confirmation fails in step 704, the method ends in step 706. However, if identity is confirmed, treatment begins in step 708.

Treatment begins with the activation of the treatment apparatus in step 710, and patient biometric data is monitored in step 712, and compared to patient biometric data tolerances in step 714. If the treatment is complete as determined in step 716, the treatment ends in step 736. If the treatment is not complete, the treatment continues in step 718 and the patient's physical data is monitored in step 720. If the patient physical data is within tolerance in step 722, treatment continues with return to step 712. If the patient physical data is not within tolerances, the physical data is analyzed in step 724 to determine if it is within a safe range. If so, the patient is provided feedback in step 732 to facilitate position self-correction, and the technician is alerted in step 734 of the position violation, and method 700 returns to step 720 for continued monitoring.

If the physical data is outside the safe range as determined in step 724, the technician is alerted of the safety issue in step 726, the treatment apparatus in interrupted in step 728, and the treatment ends in step 730.

If it is determined in step 714 that the patient biometric data is not within the preset tolerances, it is determined in step 738 whether the biometric data is outside the safety range. If safe, the technician is alerted in step 740 of the biometric error, and treatment is adjusted in step 742, and the virtual reality application may increase patient focus in step 746, or the virtual reality application may adjust the program or game to return the patient biometric readings t within range in step 748. Once these corrective steps have been taken, method 700 returns to step 712 for continued monitoring.

If the biometric data as measured is unsafe as determined in step 738, the technician is alerted in step 750 and the treatment apparatus is interrupted in step 752 and the treatment ends in step 754.

In a preferred embodiment of the method of the present invention, on the day of treatment, a typical treatment process is as follows:

a) Patient is set up on the treatment table;

b) imaging scan the patient's face and record voice to verify it is the correct patient. This "Time-out" is the requirement for all treatment centers to ensure proper patient identification and treatment;

c) Patient puts on the virtual reality goggles and headset, and the sensors are attached to the patient;

d) imaging scan and assist patient/technician to make adjustment so patient is in the reference position;

e) This current position is "captured" or recorded together with biometric sensor data;

f) At this time, the virtual reality game is turned on and operator will leave the treatment room and go to the treatment console;

h) Operator will check with the position monitor and biometric monitor to see they are within limit ("Green light");

i) Operator will turn on the treatment machine and informed patient via headset;

j) Position and biometric sensor monitor are continuously feeding signal and display via monitor:

"Green Light" (position is good);

"Yellow Light" (small deviation can be corrected by patient, treatment can be continued, and technician is stand by to pause treatment if necessary; and "Red Light" (Major deviation—treatment must be paused automatically. Adjustment must be made by patients first, then technician if needed before treatment can be resumed;

k) If respiration gating feature is used, one more step is added to have patient holding their breath to certain level and go by Green, Yellow, Red light system; and l) Treatment completed.

What has been described here are exemplary methods capable using the Virtual Reality Medical Application System of the present invention. It is to be appreciated that other variations of these methods may be achieved using the present invention, and no limitations as to these methods are intended by the few exemplars presented herein.

Figure 10:
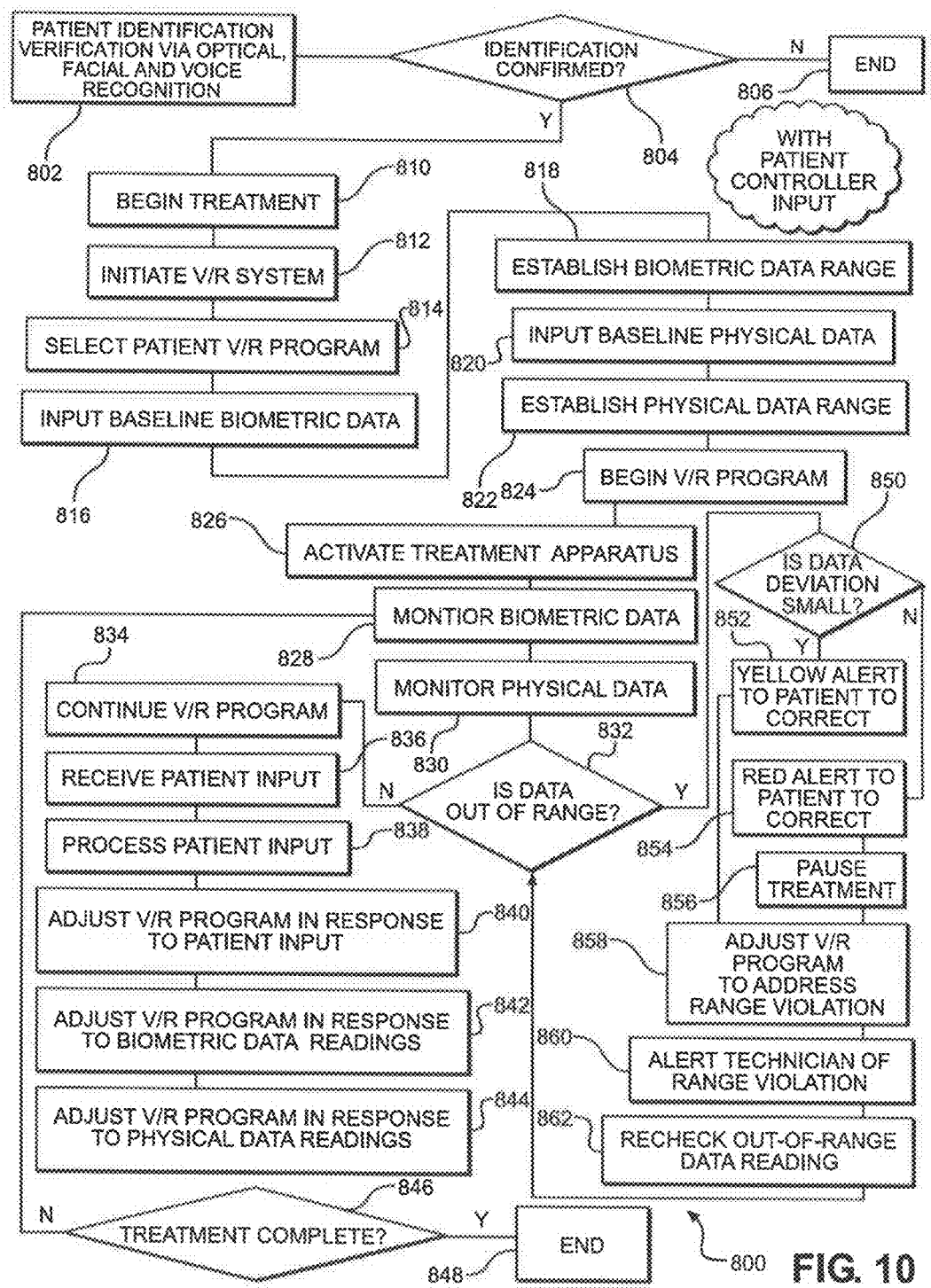
FIG. 10 is a flow chart representing the beginning of treatment of FIG. 6 using patient controller input, and includes the verification of patient identity, the activation of the medical treatment apparatus, and the subsequent monitoring and evaluation of position and biometric data for compliance and safety, providing a patient with biometric and positional feedback to assist with correction, receipt of patient input data, and modification of the virtual reality program to facilitate such patient correction.

Referring now to FIG. 10, a flow chart generally designated 800 representing the beginning of treatment of FIG. 6 using patient controller input, and includes the verification of patient identity in step 802. If the identity cannot be confirmed in step 804, the treatment ends in step 806. If identity is confirmed, treatment begins in step 810, and the virtual reality system is initiated in step 812, and the patient virtual reality program is selected in step 814.

The patient baseline biometric data is input in step 816, and the biometric data range for the treatment is established in step 818. The baseline physical data is input in step 820, and the physical data range is established in step 822. The virtual reality program begins in step 824 followed by the activation of the treatment apparatus in step 826.

Biometric data is monitored in step 826, and physical data is monitored in step 830. If data is within range as determined in step 832, the virtual reality program continues in step 834 to receive input from the patient in step 836, and to process the patient input in step 838. As the virtual reality continues, the program adjusts in response to patient input in step 840, and adjusts in response to biometric data readings in step 842, and adjusts in response to physical data readings in step 844. If treatment is complete as determined in step 846, treatment ends in step 848; otherwise, control returns to step 828 to continue monitoring biometric data.

If the data measured is out of range as determined in step 832, the data deviation is determined in step 850. If the deviation is small, a yellow alert is provided to the patient in step 852, and the virtual reality program adjusts to address the range violation to provide the patient with self-correction guidance. If the data deviation is not small as determined in step 850, a red alert is given to the patient in step 854, and the treatment is paused in step 856, and the virtual reality program is adjusted to address the range violation in step 858.

Once the virtual reality program has been adjusted, the technician is alerted of the range violation in step 860, and the out-of-range data is rechecked in step 862. Again, in step 832, it is determined if the data is out of range, and the method continues.

Figure 11:
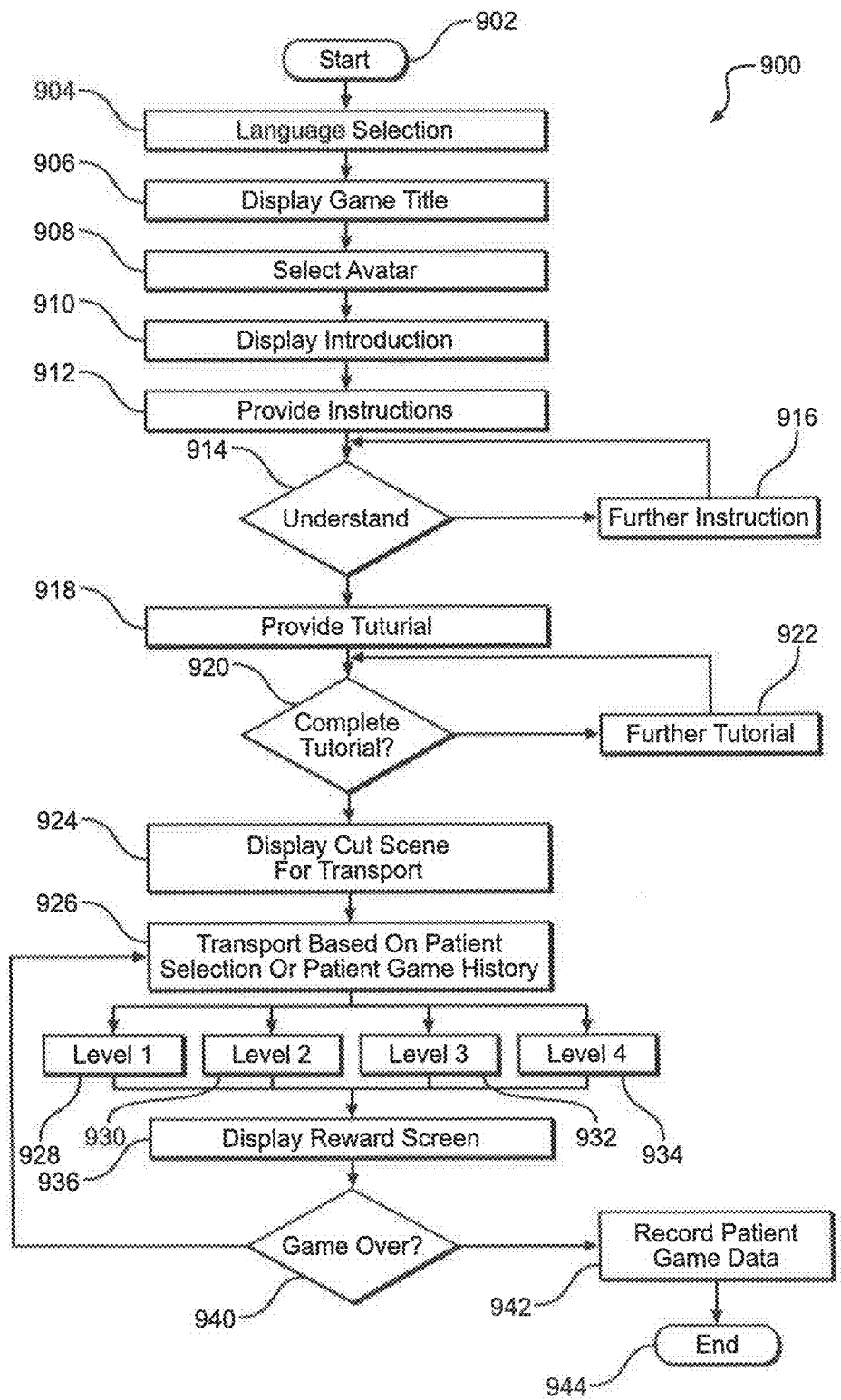
FIG. 11 is an exemplary flow chart depicting operation of the game interface of the Virtual Reality Medical Application System of the present invention, and includes a language selection, display of a game title and avatar selection, providing operating instructions to the patient confirming the patient's understanding, providing a tutorial, and then providing a patient interactive game sequence intended to assist a patient to minimize movement during the procedure, and providing patient incentives for being still including game token rewards and scoring.

Referring now to FIG. 11, an exemplary flow chart is generally designated 900 and depicts operation of the game interface of the Virtual Reality Medical Application System of the present invention. Method 900 begins in step 902, and a language is selected in step 904. This language would correspond to the patient's most familiar language, thus providing a sense of comfort to the patient during the treatment. Once language is selected, the game title is displayed in step 906. As will be shown below, this game title may correspond to virtually any game which incorporates patient stabilization features, and is age appropriate for the patient being treated.

A patient avatar is selected in step 908, and the introduction is displayed to the patient in step 910, and instructions are provided in step 912. If the patient does not understand as determined in step 914, then addition instruction is given in step 916. If the patient understood the instructions, a tutorial is provided in step 918. If the patient does not adequately understand or complete the tutorial, addition tutorial is provided in step 922. Once the patient completes the tutorial successfully as determined in step 920, step 924 displays the "cut scene" to transport the patient avatar to the various game environments as determined in step 926, such as determined by the patient's prior game history or patient age, for example.

The patient avatar may be sent to any number of levels or worlds, such as level 1 928, level 2, 930, level 3, 932, or level 4, 934. Once on the particular level or world, the patient's reward screed is displayed in step 936. If the game is over, as determined in step 940, the patient game data is recorded in step 942, and the game ends in step 944. if the game is not over, control returns to step 926 and the game continues as the patient avatar navigates through the various levels, various game worlds, and successfully completes each challenge within the game. Preferably, the game duration would correspond to the duration of the patient's treatment such that the attention of the patient is drawn fully into the virtual reality world.

Exemplary Game and User Interlace

Figure 12:
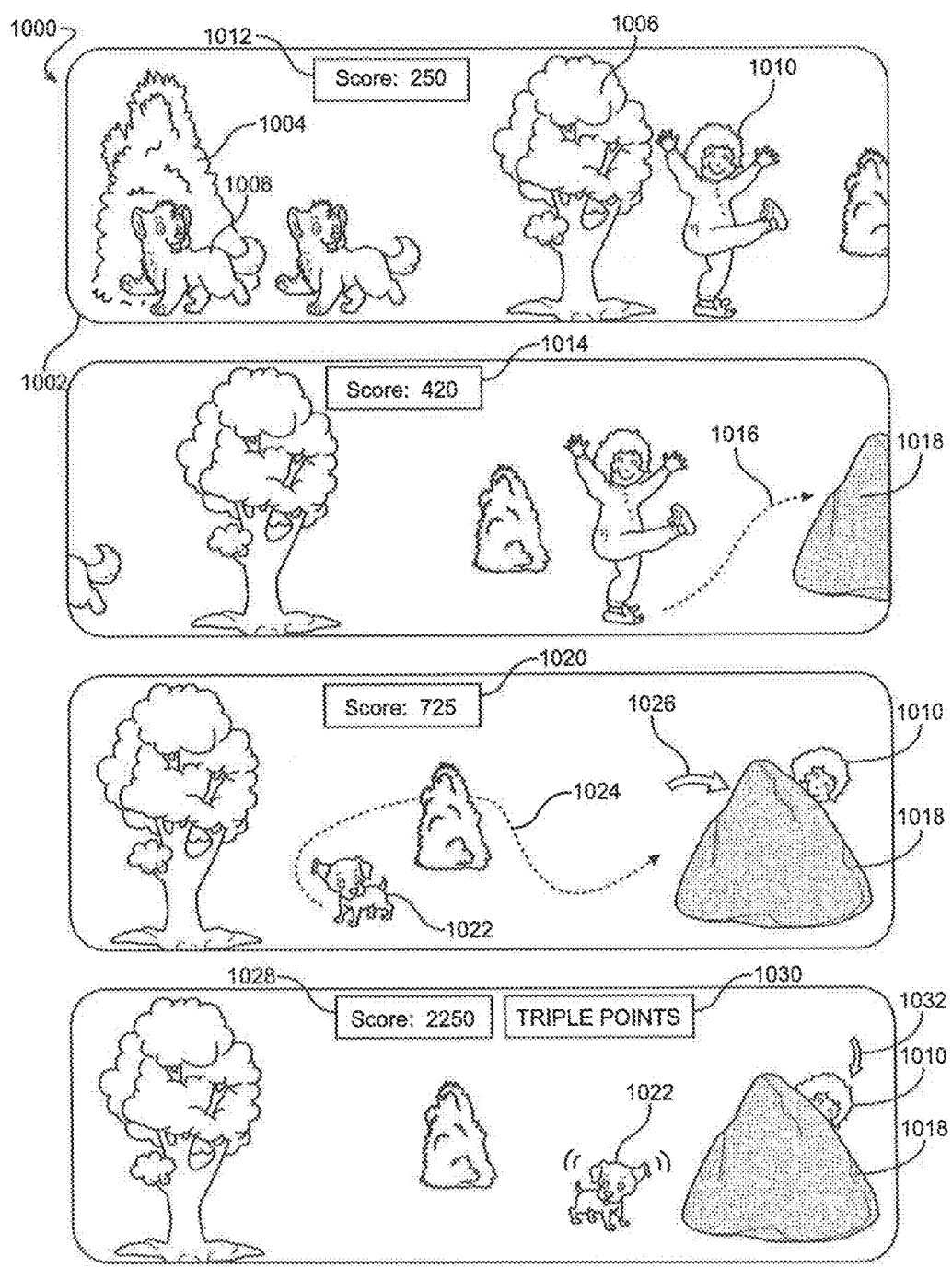
FIG. 12 is an exemplary view of the patient's display image in the head mounted display during the operation of the Virtual Reality Medical Application System of one embodiment of the present invention and depicting various video progressions of a child avatar playing in a park and being sought out by a friendly puppy, scoring points for successful avoidance of the exuberant puppy, and a high scoring segment corresponding to a critical treatment period requiring the patient to remain still as the puppy continues to seek the avatar.

A number of exemplary game interfaces are presented herein. For instance, FIG. 12 is an exemplary view of a simple virtual reality game. A series of the game display images 1000 are shown as presented in the head mounted display during the operation of the Virtual Reality Medical Application System of the present invention. These video progressions include an image 1002 filled with environmental surroundings such as trees and shrubs 1004 and 1006, and local animals 1008. A child avatar 1010 is shown playing in a park. A score panel 1012 keeps track of the patient's game score. In subsequent frames, the avatar 1010 can move throughout the display as shown by arrow 1016, and can advance around and through the surroundings, such as behind rock 1018. In a simplified example, patient avatar 1010 is being sought out by a friendly puppy 1022 which traverses through the display image in path 1024 in friendly pursuit of the patient avatar that hides in direction 1026 behind rock 1018. Patient feedback can be used to make certain that no movement occurs for fear of alerting the puppy 1022 of the avatar's location. Scoring points can be achieved by the successful avoidance of the exuberant puppy 1022. In circumstances corresponding to a critical treatment period requiring the patient to remain still, a high scoring segment 1030 may be used which includes the puppy continually approaching the avatar which ducks in direction 1032 behind the rock to avoid detection.

This simple example of the Virtual Reality Medical Application System of the present invention provides for the virtual reality system to provide physical feedback to the patient during treatment to maintain proper positional placement. Moreover, the biometric feedback data from the patient monitoring can be incorporated into the virtual reality system to change the avatar environment, increase or decrease patient focus, in order to increase focus and decrease stress on the patient during treatment.

Game Description for FIGS. 13 Through 21

FIGS. 13 through 22 depict an alternative sequence of a game displayed in the Virtual Reality Medical Application System of the present invention, which is an animated story in which a patient-linked avatar helps a dinosaur to retrieve its eggs from an egg-stealing robot by riding a flying skateboard throughout a virtual world to retrieve the stolen eggs, and requires the avatar to remain motionless during flight to avoid losing the trail of the stolen eggs, or dropping any retrieved eggs, thus returning all of the stolen eggs safely to the grateful dinosaur.

Figure 13:
FIGS. 13 through 22 depict an alternative sequence of a game displayed in the Virtual Reality Medical Application System of the present invention, which is an animated story in which a patient-linked avatar helps a dinosaur to retrieve its eggs from an egg-stealing robot by riding a flying skateboard throughout a virtual world to retrieve the stolen eggs, and requires the avatar to remain motionless during flight to avoid losing the trail of the stolen eggs, or dropping any retrieved eggs, thus returning all of the stolen eggs safely to the grateful dinosaur.

An exemplary title page is shown in FIG. 13, and generally designated 1020. FIG. 13 includes an exemplary title page including a game name, and representative game graphics to introduce the patient to the game environment Specifically, display 1020 depicts an animated world, full of vibrant colors and friendly detail which will appeal to the age group for the patient being treated. Understandably, the genre of the virtual reality environment, and the particular details of the game presented in that environment will change depending on the age of the patient, and the patient's ability to understand and interact with more complicated games. Indeed, the present invention contemplates generally utilizing virtual reality technology with attractive computer graphics to make a game which can bring kid patients into a virtual world and make immerse in it and stay still for no less than 30 minutes when they're having the radiation treatment.

Exemplary features of a virtual reality environment of an embodiment of the present invention include:

Kid patients, ages from 3-10 (older kids may need to be considered also)
Target platform: Personal Computer (PC) or Laptop
Display hardware: Oculus Rift II or similar goggle
Input device: N/A
Extra device: monitor camera
Game engine: Unity 3D In the exemplary game depicted in FIGS. 13 through 21, Dr. Patel is a crazy almighty scientist and dinosaur maniac. His ambition is to build a dinosaur park for children on the earth to represent the fantastic era of dinosaur. By his research, he found there's a planet (D-Planet) in the universe which has an ecological environment similar to the one the earth used to have back to millions years ago and has dinosaurs active on it. Thus he wants to get the kid (player) transported by a spaceship and use the "Aero Skate Board" he created to collect different types of dinosaur eggs by all mean. There are multiple isolated islands on D-Planet. On each island lives a certain type of dinosaur; various islands may be provided, each with its only variety of dinosaurs to be saved.

in order to help Dr. Patel to build a dinosaur park on the earth, the child patient avatar is chosen to be transported to another planet named "D-Planet" which has an ecological environment similar to the one the earth used to have back to millions years ago. There're multiple islands on "D-Planet" and on each island lives a type of dinosaur. The ultimate task for the chosen child avatar is to utilize a special equipment named "Aero Skate Board" and by all means to search and collect eggs of different types of dinosaurs on different islands and bring them all back to the earth.

Because one target audience are 3-10 years old child patients, it's important to create a virtual world that can let them fully immerse in for 30 minutes, so the art style in general has to be cute, cartoonish with colorful and bright palettes. Here below are some examples of look and feel of a preferred embodiment of the present invention depicting characters, dinosaurs, items and environments (level)

For instance, if the child patient is a boy, then the game system will assign this boy avatar to him as his virtual identity. He will play the role as the little adventurer chosen by Dr. Patel and accomplish his mission of dinosaur eggs collecting on D-Planet. Alternatively, if the child patient is a girl, then the game system will assign this girl avatar to her as her virtual identity. She will play the role as the lithe adventurer chosen by Dr. Patel and accomplish her mission of dinosaur eggs collecting on D-Planet.

Figure 14:
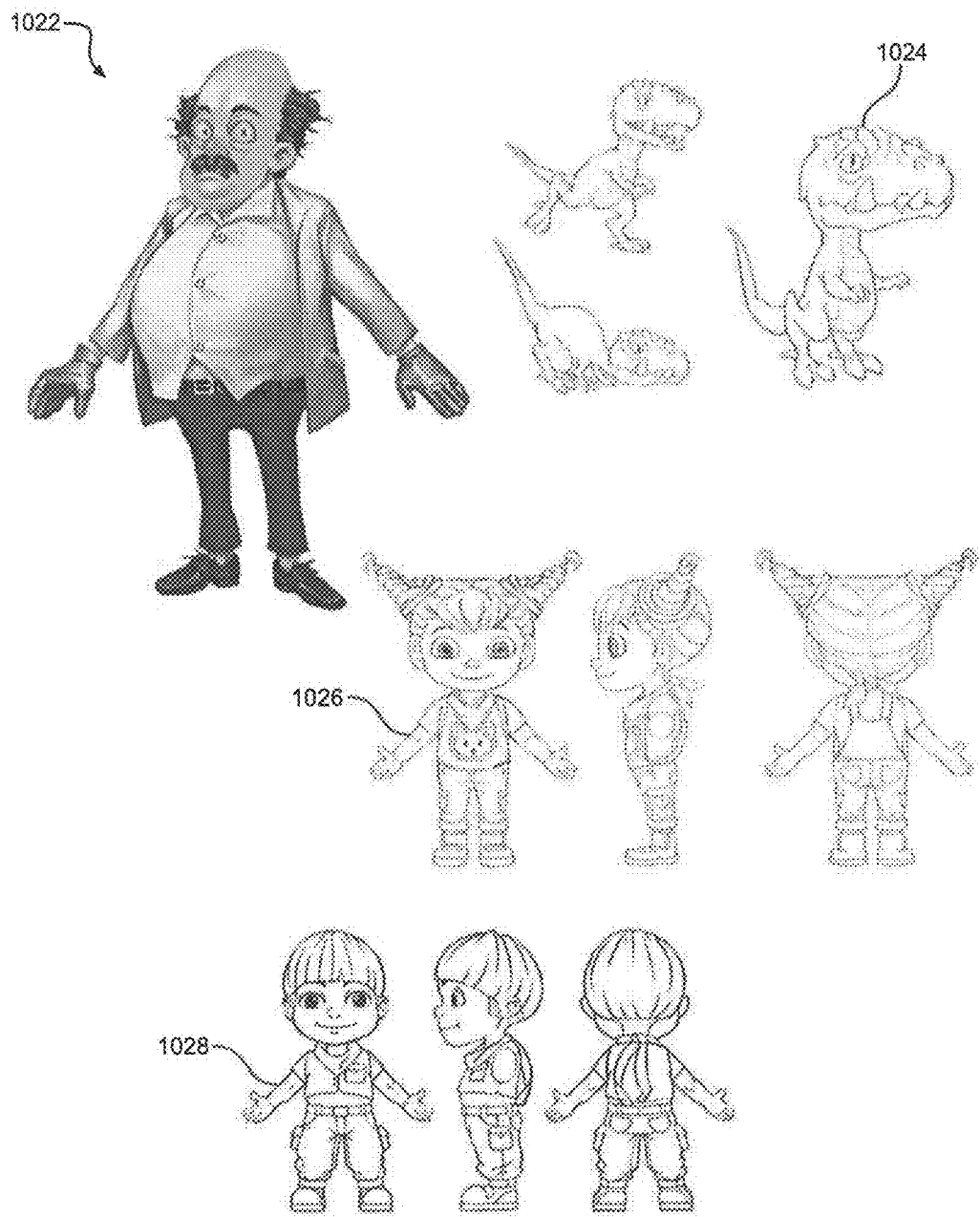

FIG. 14 is an exemplar of various game avatar characters. For instance, eccentric doctor Patel 1022, a dinosaur 1024, a girl patient avatar 1026, and a boy patient avatar 1028 that can be used in the game of the Virtual Reality Medical Application System of the present invention to accomplish the virtual reality environments that capture the child patient's imagination during his or her treatment.

Figure 15:
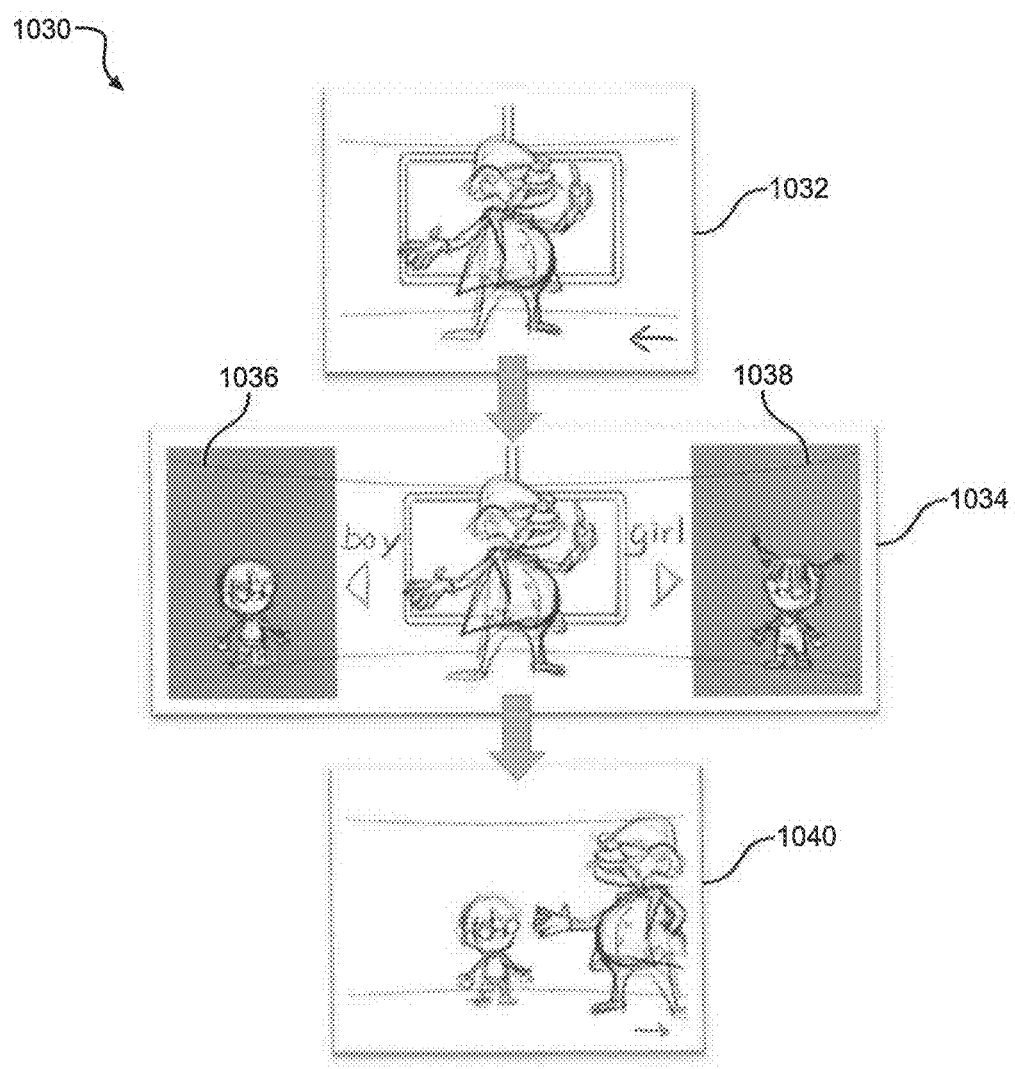

FIG. 15 is an exemplary avatar selection screen in which an eccentric doctor selects a boy or girl (patient) avatar, such as by the patient rotating his or her head in the direction of the desired avatar, such as turning the head right to select the girl avatar, or left to select the boy avatar, with the selection being advanced to the next game screen;

Dr. Patel walks into the screen from right (screen 1032).
Makes self introduction.
Inside Dr. Patel's Lab (a rounded hall)
A big screen hangs from the ceiling of the lab.
Dr. Patel asks patient to identify gender (Screen 1034).
Boy turns head to left (Screen 1036)/Girl turns to right (screen 1038).
Grey area can only be seen when patient turns his/her head when identified.
Dr. Patel walks towards boy (screen 1036).
Boy activated when Dr, reaches him.
Dr. leads boy return to center of screen (Screen 1040).
Patient needs to turn his head back.
Camera moves towards to show the big screen.
Dr. Patel starts to introduce the mission.
D-Planet map shows on the screen (turning slowly).
Boy faces towards the screen and listens.

Using the virtual reality environment, a variety of gameplay options are available, and the specific examples presented herein are not to be construed as any limitation of the present invention.

Gameplay Option 1

In each level, the chosen child avatar must hide behind a certain object and keep still in the game scene for a certain period of time (60 sec-90 sec) when the Egg Collector is searching and collecting dinosaur eggs. If the patient moves any part of the body during the period of time then the patient avatar will correspondingly move in the virtual reality environment, and the dinosaur parents will be aware and go to protect eggs and destroy the Egg Collector.

The Egg Collector has a countdown clock on its surface to show time countdown. If the child patient moves any part of the body, the movement will be detected by the motion monitoring system and child patient's avatar in the game will move correspondingly.

The Egg Collector will also stop collecting eggs for a few seconds. If the child patient moves 3 times during the period of time, the egg collection mission failed and the patient avatar will need to re-do the same mission.

The patient avatar will get rewarded with a bronze egg or saver egg or gold egg based on the behavior in the finished level. Egg reward of each level has different/unique design, and given that many treatments require multiple sessions, it is conceivable that a patient will be able to collect many different rewards over the course of treatment.

Gameplay Option 2

Mother dinosaur lost 5 eggs in each level and it's hard for her to find them back because she has other eggs need to be taken care of. The chosen kid volunteered to find all 5 eggs back.

Riding a hi-tech "aero skateboard" and carrying an egg-protector on the back, the avatar starts the journey in the level to look for lost eggs. He/She needs to standing on the skateboard by keeping balance (in order to make it flying smooth and stable). If the child patient moves any part of the body, the movement will be detected by the monitor camera, body position, and patient's avatar in the game will move correspondingly and this will make the skate board unbalanced.

If the child patient moves 3 times during the period of time, $1^{st}$ time caution light on the tail of skateboard will turn into orange and flickering; $2^{nd}$ time caution light on the tail of skateboard will turn into orange and flickering rapidly; $3^{rd}$ time mission failed.

The patient avatar will receive rewards from the mother dinosaur with an egg if the level is completed. Each egg reward of each level has different/unique design (to indicate a certain type of dinosaur).

Figure 16:
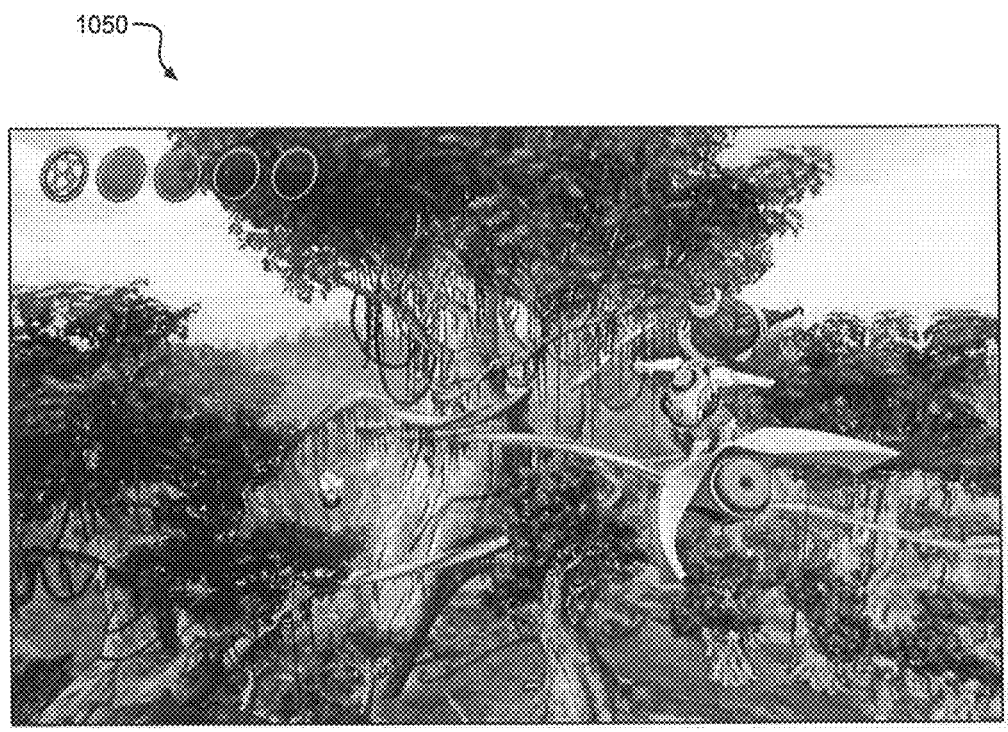

FIG. 16 is an exemplary display 1050 of a game within the Virtual Reality Medical Application System of the present invention depicting the patient avatar on a flying skateboard and traveling through a virtual forest in pursuit of lost dinosaur eggs. This is an example of a preferred embodiment of the virtual reality environment.

Figure 17:
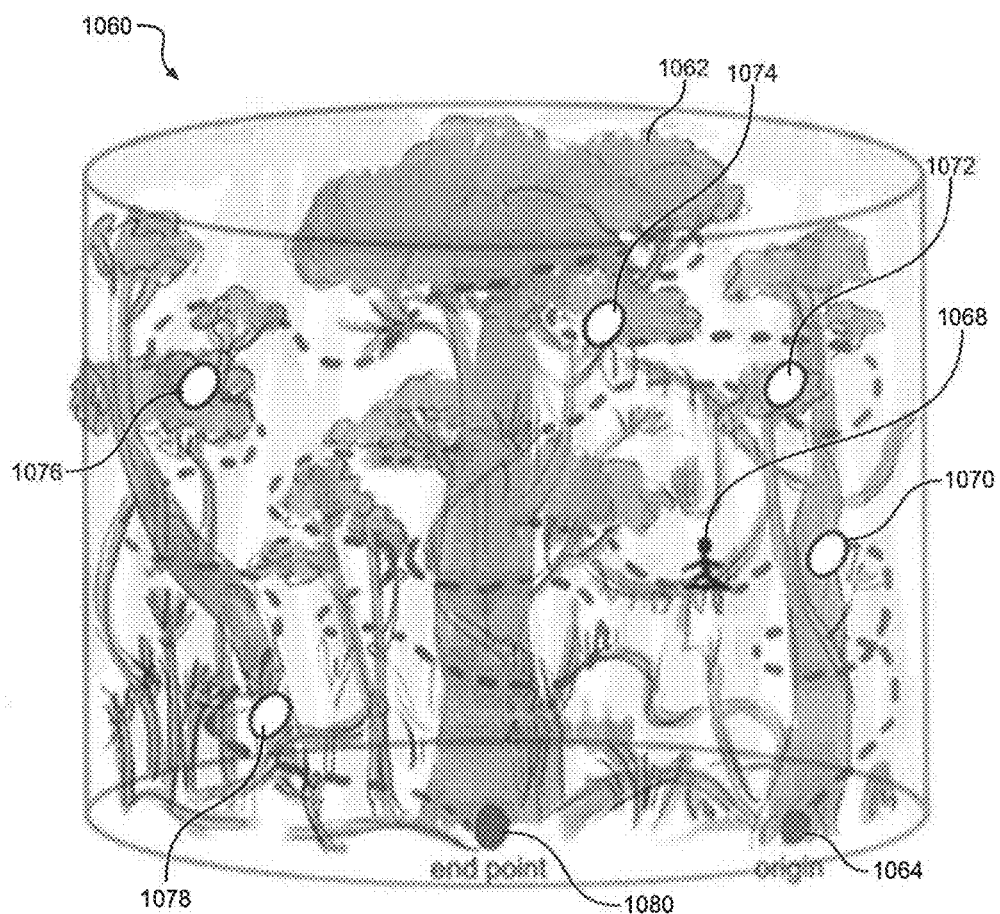

Referring now to FIG. 17, an exemplary map of a game within the Virtual Reality Medical Application System of the present invention is shown and generally designated 1060. A representative forest 1062 with colorful topography, and the advancement of the patient avatar from an origin 1064 to an end point 1080 is designed to allow the avatar 1068 to gather the stolen eggs 1070, 1072, 1074, 1076, and 1078 from the forest. In this version, the patient avatar will ride the skateboard and start egg collecting from point green 1064 and end up at point red 1078 by the route line showing in the image on the left. In this preferred embodiment, the route is set up by program and it cannot be changed. Other embodiments feature a dynamic route determined by the random placement of the eggs throughout the forest 1062, such that each experience for the patient will vary.

The estimated time of finishing the level will be around 4~5 to 10 minutes. If the child patient moves his or her body during the game and cause the dropping or loss of any eggs, then the level will restart from the very beginning.

Figure 18:
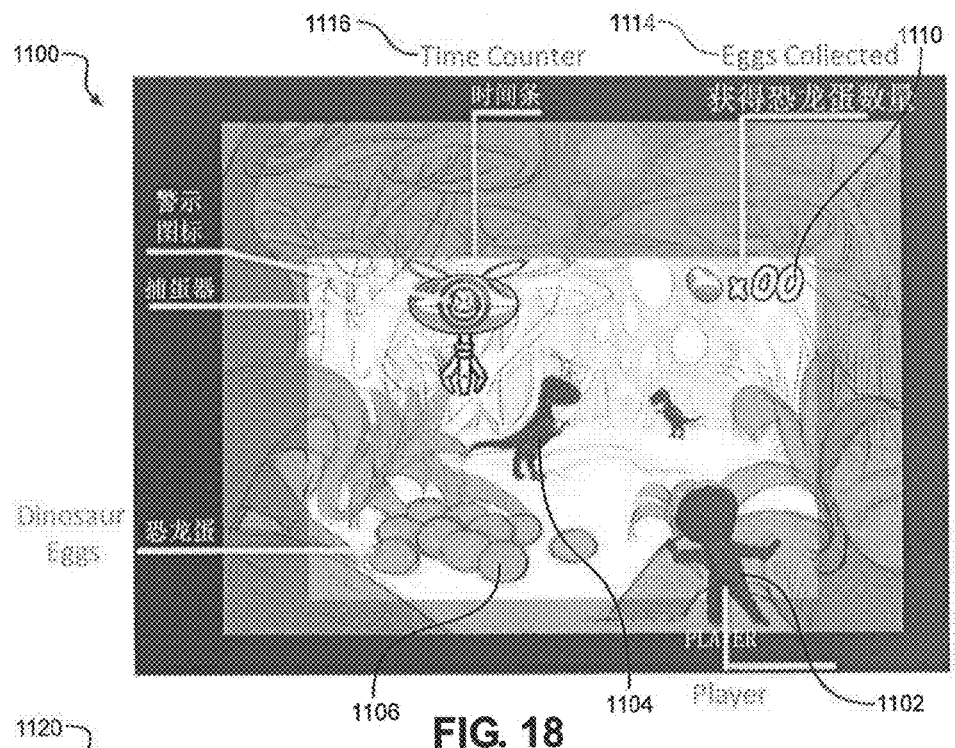

FIG. 18 is an exemplary display 1100 of the game showing the patient avatar 1102, the dinosaurs 1104, a number of eggs 1106, the egg-stealing robot 1108, with the patient avatar 1102 hiding from the robot 1108 in order to avoid detection to protect the dinosaur eggs.

A number of game statistics may be displayed on image 1100, including egg value 1110, eggs collected 1114 and time counter 1116. This data provides the patient with information related to his or her current score, the duration of the game, and the progress through the game session.

Figure 19:
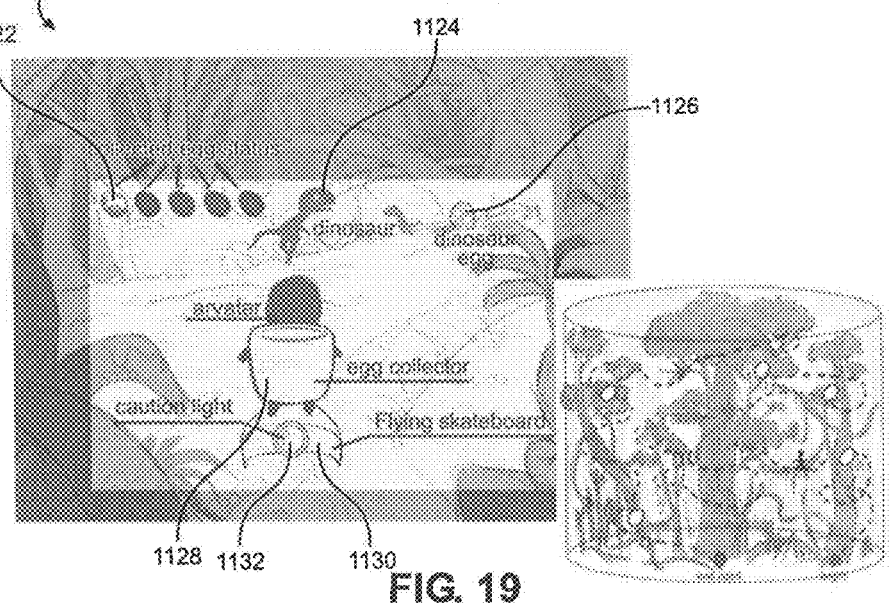

FIG. 19 is an exemplary display 1120 of the game showing the patient avatar 1128 riding a flying skateboard 1130 through the virtual forest environment in search for stolen dinosaur eggs 1126, and providing a patient with a motion status indicator light 1132 on the skateboard corresponding to patient movement measurement feedback to the patient, such as green for good, yellow for minimal patient motion detected, and red for too much motion detected. An exemplary map 1134 identifies where the patient avatar 1128 is within the virtual forest path. Also depicted in this view is the number of eggs collected 1122, and a dinosaur 1124 to be avoided.

The image on the bottom shows the scene the child patient will see in the virtual reality goggles when the game starts. For instance, five dinosaur eggs can be seen on the way (determined by the route set up) and the skateboard will lead the way to it automatically. Once a dinosaur egg is collected, an egg-figured space on the top left screen will be filled with an egg 1122 icon correspondingly.

Figure 20:
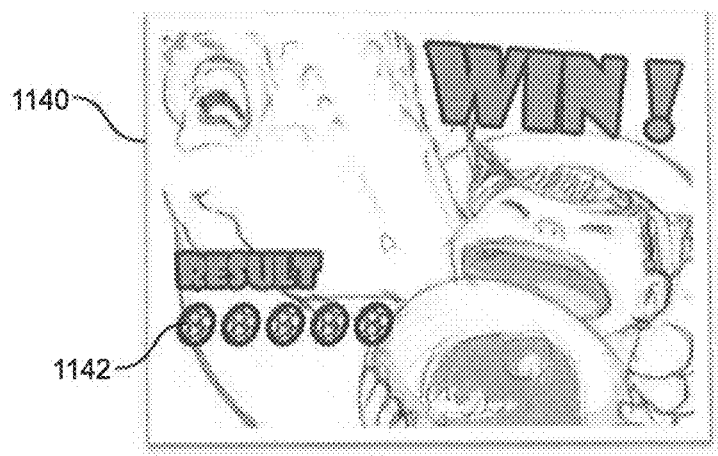
Figure 21:

At the conclusion of the game session, a representative game end screen is shown in FIGS. 20 and 21. These screens report the patient's success in collecting all of the stolen eggs from the virtual forest The FIG. 20 screen 1140 shows after current level be completed successfully. "Result" shows the number of dinosaur eggs 1142 that were saved in the completed level. "Reward" shows the reward egg (the certain type of egg) player gets from dinosaur mother. Alternatively, the FIG. 21 screen 1150 is representative of the patients' failure to collecting all of the stolen eggs 1152 from the virtual forest. This screen shows after the player failed to completed current level. System will automatically switch back to current level and let player play it again. Neither "Result" nor "Reward" shows on this screen.

Figure 22:
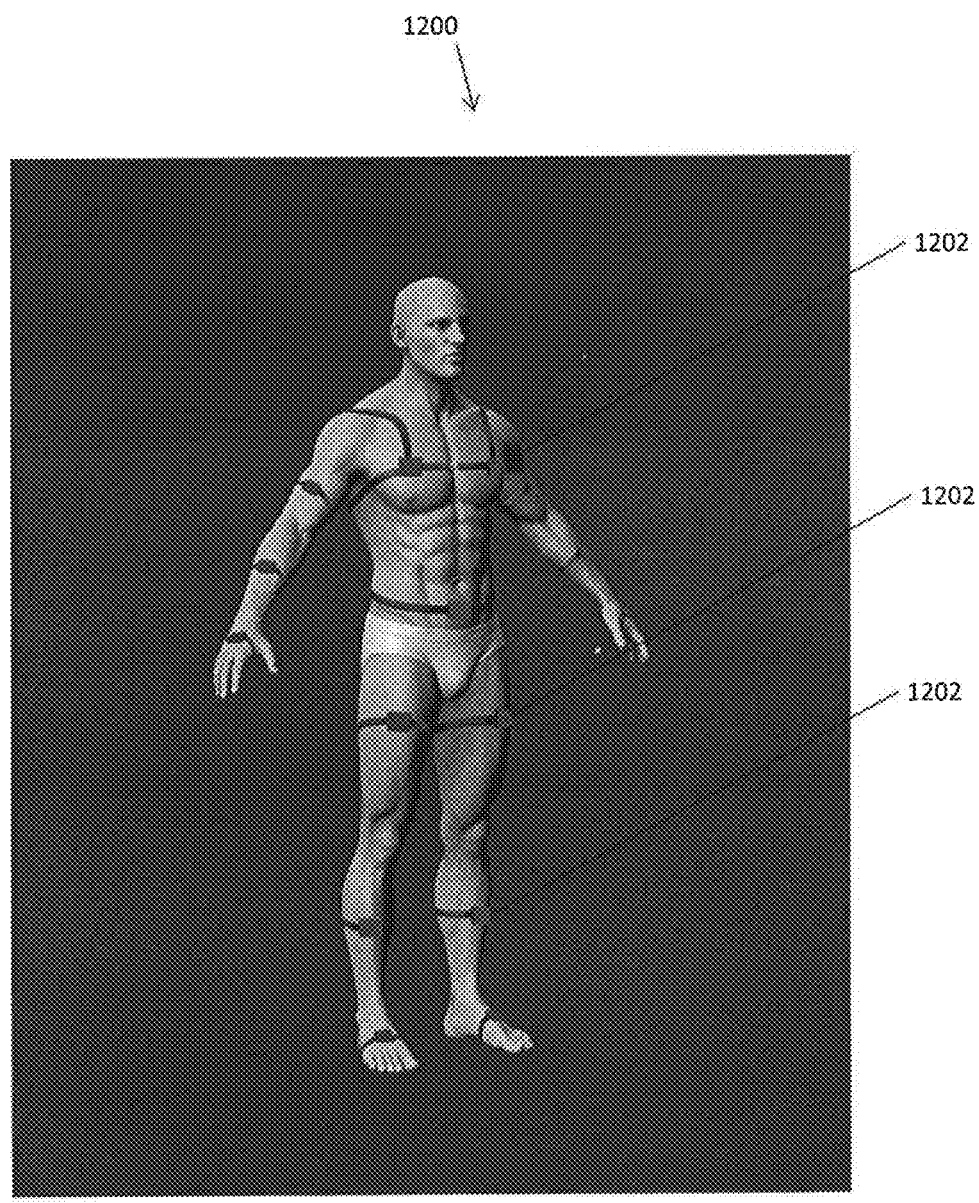

Referring to FIG. 22, a representative display of the array of IMU for body motion detection is shown and generally designated 1200. Each IMU 1202 includes the detectors necessary to sense the inertial movement of the patient. This data is relayed wirelessly to the system of the present invention in order to communicate real-time position, and dynamic changes in position, to the technician or health care provider in order to accomplish the treatment protocol.

Figure 23:
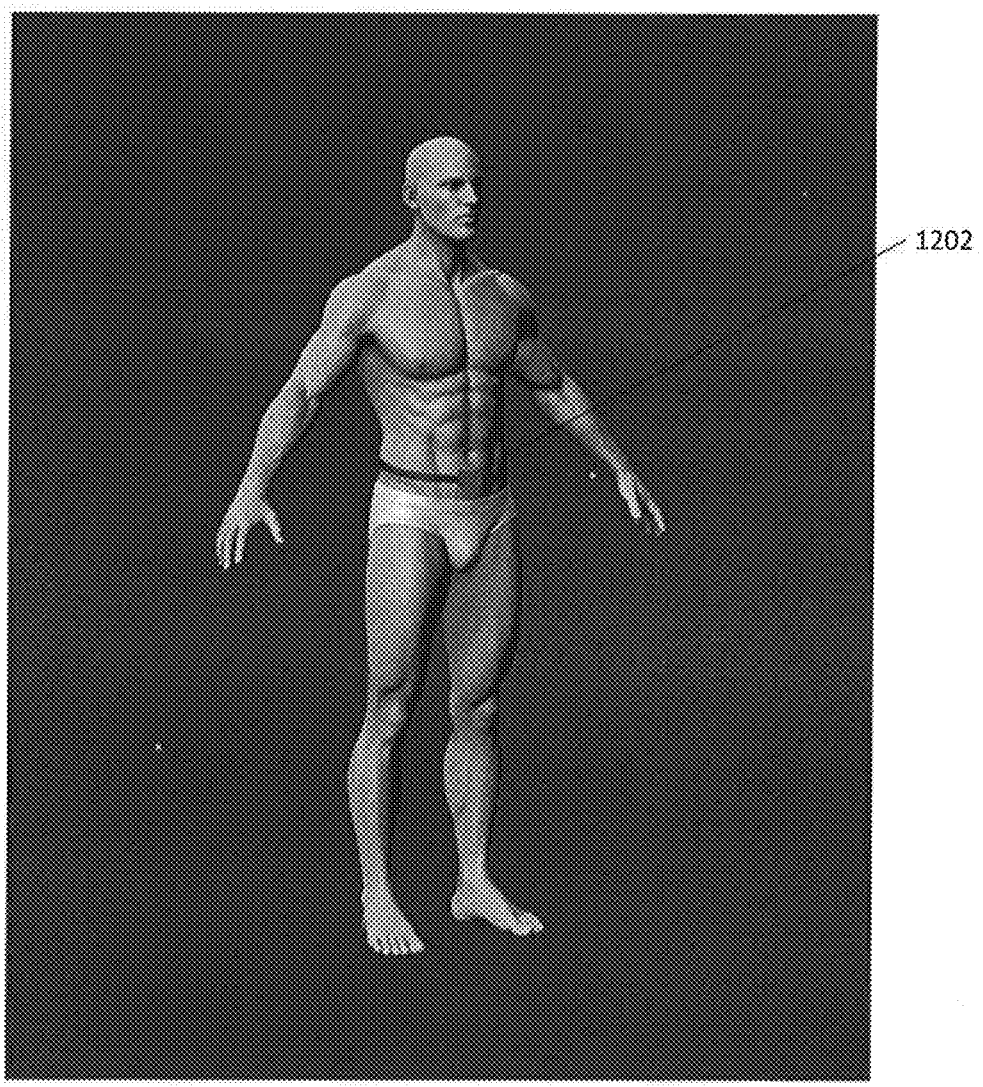
FIG. 23 is a representative display of the IMU for the respiratory gating application.

FIG. 23 is a representative display of the IMU for the respiratory gating application showing the placement of a single IMU on the abdomen of a patient. From this Figure, it can be appreciated that any variety and placement of IMU devices are fully contemplated in this invention, and can be configured to provide the technician or medical care provider the positional information required to provide safe, effective and repeat procedures.

Figure 24:
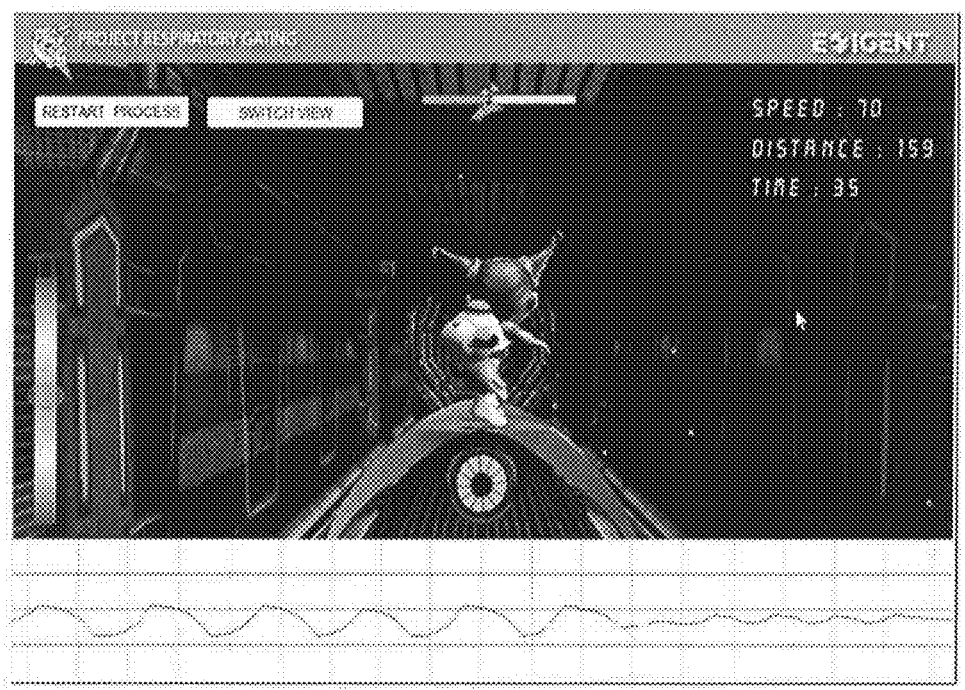
FIG. 24 is an exemplary display of the game showing how the game can assist the patient in holding their breath and breathing properly for respiratory gating application.

Another embodiment of the invention is the respiratory gating application. FIG. 24 is an exemplary display of the game showing how the game can assist the patient in holding their breath and breathing properly for respiratory gating applications. The application starts with a screen option where the technician has to record the maximum and the minimum breathing value of the patient. The IMU motion sensor is strapped on the chest of the patient where the maximum breath-in and breathe-out can be recorded The patient is asked to breath in at a maximum point (maximum inspiration) and the technician records the value. Similarly the patient is asked to breathe out maximum breath volume to record the breathe-out value (maximum expiration). These values are stored in the database which will be used during the game.

As shown in the lower portion of FIG. 24, the position of the IMU during a patients breathing is recorded and displayed for the technician or medical care provider to gauge the patient's breathing, and to verify that the patient breathing pattern is gated according to the game stimulus, and corresponding to the treatment being provided to the patient.

In a preferred embodiment, the game incorporated into the present invention is about a girl on a skateboard who travels inside a sci-fi tunnel. When the patient breathes-in, the skateboard moves up and when he/she breathes out the skateboard moves down. The values from the sensors are linked to the movement of the skateboard. The patient should not breathe more than the value recorded as the skateboard might hit the top of the tunnel and slows down the skateboard or he/she should not breathe out more since the skateboard might hit the floor and slows it down.

The ultimate goal of the game is to avoid hitting the tunnel and cover a maximum distance within the prescribed time of 45 seconds to 1 minute. Game points will be awarded on how long the breath is held+m inimal chest move up and down and the speed. Once the patient treatment is complete, the virtual reality environment returns the patient to the real world environment gradually in order to provide a smooth transition from the virtual reality environment and minimize stress upon the patient.

The Virtual Reality Medical Application System presently described herein is capable of obtaining the objects of the present invention. The particular preferred embodiments that have been presented herein are merely exemplary of preferred embodiments, but various alternative combinations of the features and components of the present invention may be constructed and are fully contemplated in the present invention.

What is claimed is:

1. A method for monitoring and controlling body movements of a patient during a radiation procedure for increased efficacy, comprising:
   providing a radiation procedure apparatus with a radiation procedure area for performing the radiation procedure;
   providing a head mounted display configured to detect head movement;
   providing an array of motion detector sensors configured to detect body movement;
   providing a plurality of biofeedback sensors configured to detect biometric data;
   providing a virtual reality console system, wherein the virtual reality console system is in communication with the head mounted display, the array of motion detector sensors, and the plurality of biofeedback sensors;

providing a radiation procedure apparatus control system, wherein the radiation procedure apparatus control system is in communication with the virtual reality console system and the radiation procedure apparatus;

positioning the patient in the radiation procedure area of the radiation procedure apparatus utilized to perform the radiation procedure;

positioning the head mounted display on the patient;

configuring the array of motion detector sensors to detect body movement of the patient;

retrieving a biometric data limits and a position data limits for the patient;

tracking a current patient position of the patient in the radiation procedure area utilizing the head mounted display to detect head movement and the array of motion detector sensors to detect body movement;

guiding the patient into a reference position in the radiation procedure area for the radiation procedure;

rendering a patient specific 3-D game by the virtual reality console system;

displaying the patient specific 3-D game to the patient through the head mounted display;

displaying the current patient position as a virtual avatar in the 3-D game, wherein the virtual avatar is controlled by the current patient position;

rendering sound to the patient with a noise-cancellation headphone and a microphone system in the head mounted display to provide a 3-way communication between the patient, the radiation procedure apparatus control system, and the virtual reality console system;

performing the radiation procedure;

sensing current biometric data of the patient and comparing the current biometric data with the biometric data limits during the radiation procedure;

communicating the current biometric data of the patient to a healthcare provider through the radiation procedure apparatus control system;

displaying a current avatar position of the avatar in the patient specific 3-D game to keep the patient in a predetermined position to improve efficacy of the radiation procedure; and providing cues through patient specific 3-D game with the avatar to the patient to adjust the patient's position to the reference position to improve efficacy of the radiation procedure, said cues comprising feedback via the avatar, pausing the patient specific 3-D game, commands from a game character, negative reinforcement in the patient specific 3-D game, and positive reinforcement in the patient specific 3-D game.

2. The method of claim 1, comprising generating a virtual simulation of real life scenery.

3. The method of claim 1, comprising rendering images of a procedure that the healthcare provider wants to share with the patient.

4. The method of claim 1, comprising detecting one or more of: blood pressure, heart rate, EEG, and EKG.

5. The method of claim 1, comprising performing gesture recognition, facial recognition and voice recognition with the virtual reality console system.

6. The method of claim 1, comprising providing treatment for one of: radiation therapy, brachytherapy, Computed Tomotherapy (CT), Positron Emission Tomography (PET), Magnetic Resonance Imaging (MRI), angiography, biopsy and endoscopy.

7. The method of claim 6, comprising sharing clinical information from medical diagnostic body scan, angiography, or endoscopy with the patient using the multimedia interaction.

8. The method of claim 1, comprising playing a game that negatively reinforces the patient to not move utilizing game play mechanics.

9. The method of claim 8, comprising providing levels of positive reinforcement to reward the patient for remaining still.

10. The method of claim 1, comprising
a. playing a game wearing the head mounted display;
b. provide a view into the virtual world where the patient can see the virtual avatar; and
c. tracking movement of the patient's body and when the patient moves in the real world, moving the virtual avatar in the virtual world in real time.

11. The method of claim 1, further comprising:
determining whether movements of the patient exceed the position data limits;
pausing the medical mission when movements of the patient exceed the position data limits until the position of the patient is adjusted to the reference position.

12. The method of claim 1, further comprising:
sending feedback to the patient to hold the patient's breath and maintain a predetermined chest position;
sending a signal to allow a radiation beam to turn on while the chest of the patient is in the predetermined chest position; and
timing the radiation beam based on the patient biometric data.

* * * * *